United States Patent [19]

Toda et al.

[11] Patent Number: 5,545,657
[45] Date of Patent: Aug. 13, 1996

[54] HETEROCYCLIC COMPOUNDS

[75] Inventors: Masaaki Toda, Osaka; Shuichi Ohuchida, Kyoto; Hiroyuki Ohno, Shiga, all of Japan

[73] Assignee: Ono Pharmaceutical Co., Ltd., Osaka, Japan

[21] Appl. No.: 354,899

[22] Filed: Dec. 9, 1994

Related U.S. Application Data

[62] Division of Ser. No. 8,365, Jan. 22, 1993, Pat. No. 5,401,760, which is a division of Ser. No. 700,299, May 15, 1991, Pat. No. 5,212,191, which is a division of Ser. No. 333,227, Apr. 5, 1989, Pat. No. 5,053,414.

[30] Foreign Application Priority Data

Apr. 8, 1988 [JP] Japan .................................. 63-85288

[51] Int. Cl.$^6$ ..................... C07D 207/416; A61K 31/40
[52] U.S. Cl. ............................... 514/422; 548/540
[58] Field of Search .......................... 548/540; 514/422

[56] References Cited

U.S. PATENT DOCUMENTS

| | | |
|---|---|---|
| 4,226,775 | 10/1980 | McEvoy et al. . |
| 4,412,128 | 3/1990 | Hennins .................... 514/422 |
| 4,857,537 | 8/1989 | Toda et al. . |
| 4,880,827 | 11/1989 | Tamoto ..................... 514/423 |
| 4,912,128 | 3/1990 | Henning et al. . |
| 4,956,380 | 9/1990 | Toda et al. . |
| 4,983,523 | 1/1991 | Henning et al. . |
| 4,983,624 | 1/1991 | Toda et al. . |
| 5,051,444 | 9/1991 | Tamoto et al. . |
| 5,102,877 | 4/1992 | Murate . |

FOREIGN PATENT DOCUMENTS

| | | |
|---|---|---|
| 0238319 | 9/1987 | European Pat. Off. . |
| 0268190 | 5/1988 | European Pat. Off. . |
| 0384341 | 8/1990 | European Pat. Off. . |
| 0414903 | 3/1991 | European Pat. Off. . |
| 155267 | 7/1987 | Japan . |

OTHER PUBLICATIONS

Protein Nucleic Acid & Enzyme 26(6), p. 513–523 (1980) with concise explanation.
Nippon Nogeikagaku Kaisha 58(11), p. 1147–1153 (1984) with concise explanation.
American Cyanamid Company (AT–E–255) pp. 2–3.
Europe 286927 A (Abstract).
Europe 320753 A (Abstract).
Journal of Neurochemistry, 41(1), p. 69–75 (1983).
Journal of Neurochemistry, 42(1), p. 237–241 (1984).
Science, 211(4482), p. 601–603 (1981).
J. Biochemistry, 94, p. 1179–1190 (1983).
Methods in Enzyme, M. Charton, p. 323, 330–333 (1985).
Annual Report Medical Chemistry, Sinkula, vol. 10, p. 306, 310, 314 (1975).
Heterocycles, Chemical Abstract 236699p vol. 107, 1987 p. 789.
Green, Protective Groups in Organic Synthesis, pp. 249–265 (1981).

*Primary Examiner*—Robert Gerstl
*Attorney, Agent, or Firm*—Sughrue, Mion, Zinn, Macpeak & Seas

[57] ABSTRACT

Heterocyclic compounds of the general formula:

$$R-\overset{O}{\underset{\underset{L}{\big|}}{C}}-N\overset{}{\underset{}{\diagup\diagdown}}Z \quad (I)$$

wherein, Z represents methylene group or sulfur atom,
R represents a general formula:

$$G-E-D-B-A-$$

L represents a group of general formula:

—CO—COR$^2$

—CO—R$^4$

—CO—CH$_2$—COR$^2$

—CO—CF$_2$—COR$^2$

—CO—CO—NR$^5$R$^6$ or

—CO—CH$_2$—CO—NR$^5$R$^6$ and non-toxic salt or hydrate thereof possess an inhibitory activity on propyl endopeptidase, and therefore useful, for prevention and/or treatment of amnesia.

10 Claims, No Drawings

HETEROCYCLIC COMPOUNDS

This is a a divisional application of prior application No. 08/008,365, filed Jan. 22, 1993, now U.S. Pat. No. 5,401,760, which is a divisional application of 07/700,299, filed May 15, 1991, now U.S. Pat. No. 5,212,191, which is a divisional of 07/333,227, filed on Apr. 5, 1989, now U.S. Pat. No. 5,053,414.

SUMMARY

The present invention is related to novel compounds having an inhibitory activity on prolyl endopeptidase.

More particularly, this invention is related to
1) novel heterocyclic compounds having an inhibitory activity on prolyl endopeptidase, of the following general formula:

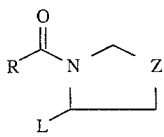
(I)

wherein, all of the symbols have the same meaning as hereafter defined
2) processes for the preparation of them, and
3) anti-amnesia agents containing them an active ingredient.

BACKGROUND

Recent advances in neuroscience are making clear the natural shape of neurotransmitter substances deeply related to memory in the brain. It is said that some of these substances are neuropeptides containing prolines.

Recovery of the memory was reported by the dosing neuropeptide containing proline to experimental amnesia rats (See Science 211, 601 (1981)).

On the other hand, it is presumed that these neuropeptide-hormones shall be metabolized by cerebral endogenous peptidases. Especially, prolyl endopeptidase (EC, 3. 4. 21. 26) might take part in these metabolisms closely (See J. Biochem., 94, 1179 (1983)).

From these facts, the studies were in progress that it should be possible to prevent or treat amnesia by inhibiting prolyl endopeptidase and suppressing the metabolism of neurotransmitters. (See Protein, Nucleic acid and Enzyme 25(6), 513(1980); Nippon Nougei Kagaku Kaishi 58(11), 1147(1984); J. Neurochem., 41, 69(1983); ibid 42, 237(1984).)

For the purpose described above, several compounds were synthesized. For example, it is clear that N-benzyloxycarbonyl-glycyl-L-prolyl-chloromethane, N-benzyloxycarbonyl-L-prolyl-prolinal strongly inhibit prolyl endopeptidase (See J. Neurochem., 41, 69 (1983)). More recently, it is disclosed that the compounds shown below are effective for the above purpose.
(i) Pyrrolidine derivatives of general formula:

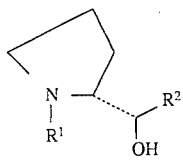
(A)

wherein, $R^1$ represents

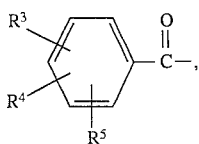

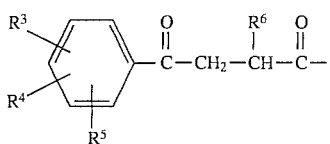

or

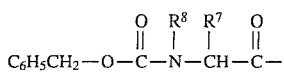

$R^2$ represents lower alkyl group, phenyl group which is unsubstituted or substituted or $-CH_2-R^{22}$.

With the proviso that, $R^3$, $R^4$, $R^5$ independently represent hydrogen atom, halogen atom, hydroxy group, lower alkyl group, phenyl group which is unsubstituted or substituted, $-CH_2R^9$, $-X-R^{10}$, $-O-CO-R^{12}$, $-NH_2$, $-NHR^{14}$ or $NR^{17}R^{18}$, with the proviso that $R^9$ represents phenyl group which is unsubstituted or substituted. X represents an oxygen atom or sulfur atom. $R^{10}$ represents lower alkyl group, phenyl group which is substituted or unsubstituted or $-CH_2R^{11}$, with the proviso that $R^{11}$ represents phenyl group which is unsubstituted or substituted. $R^{12}$ represents lower alkyl group, phenyl group which is unsubstituted or substituted or $-CH_2R^{13}$, with the proviso that $R^{13}$ represents phenyl group which is unsubstituted or substituted. $R^{15}$ represents lower alkyl group, cycloalkyl group of 5 or 6 ring members, phenyl group which is unsubstituted or substituted, $-CH_2R^{15}$, with the proviso that $R^{15}$ represents phenyl group unsubstituted or substituted.) or $-CO-R^{16}$ with the proviso that $R^{16}$ represents lower alkyl group or phenyl group which is unsubstituted or substituted $R^{17}$ and $R^{18}$ independently represent lower alkyl group or $-CH_2R^{19}$, with the proviso that $R^{19}$ represents phenyl group which is unsubstituted or substituted.

$R^6$ represents a hydrogen atom or lower alkyl group. $R^7$ represents a hydrogen atom, lower alkyl group, benzyl group, $CH_3-CH(OH)-$ or $-(CH_2)_n-R^{20}$, with the proviso that n represents an integer of from 0 to 4. $R^{20}$ represents

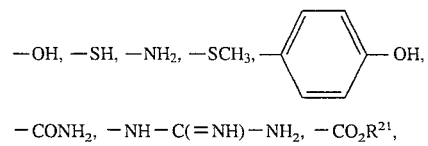

with the proviso that $R^{21}$ represents hydrogen atom, lower alkyl group or benzyl group, or heterocyclic ring group. $R^8$ represents hydrogen atom or 5-membered heterocyclic ring group together with $R^7$ and nitrogen atom and carbon atom which are neighboured. $R^{22}$ represents phenyl group which is unsubstituted or substituted. See Japanese Patent Kokai No. 62-221666, i.e., European Patent Publication No. 238319.

3 ii) Pyrrolidine derivatives of its general formula:

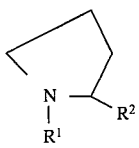
(B)

wherein, R¹ represents

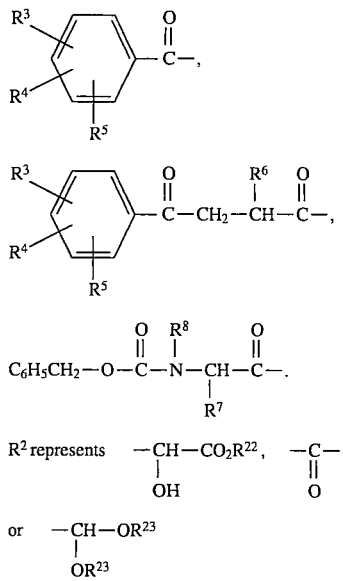

R² represents

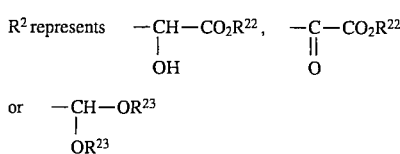

with the proviso that, $R^3$, $R^4$ and $R^5$ independently represent hydrogen atom, halogen atom, hydroxy group, lower alkyl group, phenyl group which is unsubstituted or substituted, —$CH_2R^9$, —X—$R^{10}$, —CO—$R^{12}$, —$NH_2$, $NHR^{14}$ or —$NR^{17}R^{18}$, with the proviso that $R^9$ represents phenyl group which is unsubstituted or substituted. X represents an oxygen atom or sulfur atom. $R^{10}$ represents lower alkyl group, phenyl group which is unsubstituted or substituted, or —$CH_2R^{11}$, with the proviso that $R^{11}$ represents phenyl group which is unsubstituted or substituted. $R^{12}$ represents lower alkyl group, phenyl group which is unsubstituted or substituted or —$CH_2R^{13}$, with the proviso that $R^{13}$ represents phenyl group which is unsubstituted or substituted. $R^{14}$ represents lower alkyl group, cycloalkyl group of 5 or 6 rings members, phenyl group which is unsubstituted or substituted, —$CH_2R^{15}$, with the proviso that $R^{15}$ represents phenyl group which is unsubstituted or substituted, or —CO—$R^{16}$, with the proviso that $R^{16}$ represents lower alkyl group, or phenyl group which is unsubstituted or substituted. $R^{17}$ and $R^{18}$ independently represent lower alkyl group or —$CH_2R^{19}$, with the proviso that $R^{19}$ represents phenyl group which is unsubstituted or substituted. $R^6$ represents hydrogen atom or lower alkyl group. $R^7$ represents hydrogen atom, lower alkyl group, benzyl group, $CH_3$—CH(OH)— or —$(CH_2)_n$—$R^{20}$, with the proviso that n represents an integer of from 0 to 4. $R^{20}$ represents —OH, —SH, —$NH_2$, —$SCH_3$,

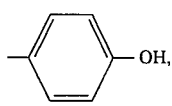

—$CONH_2$, —NH—C(=NH)—$NH_2$, —$CO_2R^{21}$, with the proviso that, $R^{21}$ represents hydrogen atom, lower alkyl group or benzyl group, or heterocyclic ring group, $R^8$ represents hydrogen atom, or 5-membered heterocyclic ring group together with $R^7$ and a nitrogen atom and carbon atom which are neighboured. $R^{22}$ represents hydrogen atom, lower alkyl group, phenyl group which is unsubstituted or substituted, or —$CH_2R^{24}$ with the proviso that $R^{24}$ represents phenyl group which is unsubstituted or substituted. $R^{23}$ represents or when $R^{23}$ and $R^{23}$ are each taken together, they represent lower alkylene group or lower alkylene group. See Japanese Patent Kokai No. 62-221667, i.e., European Patent Publication No. 238319.

The present inventors have also filed an application related to prolinal derivatives having an activity of anti-amnesia, in advance of the present application, i.e.:

(iii) Prolinal derivatives of general formula:

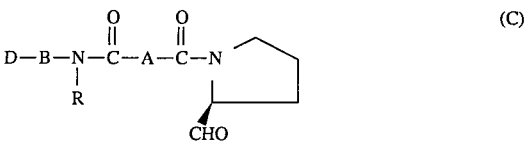
(C)

wherein A represents alkylene or alkenylene group of from 1 to 8 carbon atom(s) or a saturated hydrocarbon ring of from 3 to 7 carbon atoms, R represents hydrogen atom, phenyl group, benzyl group, alkyl group of from 1 to 8 carbon atom(s) or cycloalkyl group of from 3 to 7 carbon atoms, B represents alkylene group of from 1 to 8 atom(s) unsubstituted or substituted by phenyl group or benzyl group or a single bond, D represents carbocyclic or heterocyclic ring unsubstituted or substituted by from one to three of halogen atom, alkyl or alkoxy group of from 1 to 4 carbon atom(s), nitro group or trifluoromethyl group. See Japanese Patent Application No. 62-290631, i.e., European Patent Publication No. 268190.

COMPARISON WITH THE PRIOR ART

The compounds of the present invention of the general formula (I) are novel compounds which have new modifications.

More concretely, each groups of the compounds of the general formula from (Ic) to (If) shown below which corresponds to the group R of the compounds of the general formula (I) are new substituents. It was first found that the compounds of the general formula from (Ic) to (If) possess an inhibitory activity on prolyl endopeptidase by the present inventors.

The compounds of the general formula (Ia) and (Ib) are also novel.

The present inventors tried to modify the group D of the compounds of the general formula (C) in our application described hereinbefore. We confirmed that the compounds wherein the benzene ring was converted to another ring (including heterocyclic rings, fused rings, e.g. naphthalene, fluorence, furan etc.) also have the inhibitory activity on prolyl endopeptidase.

As the group G in the general formula (I) corresponds to the group D of the general formula (C), it is not difficult to expect that the compounds wherein the benzene ring as the group G was replaced by an other ring will possess the inhibitory activity on prolyl endopeptidase, when the compounds of the present invention wherein the group G is a benzene ring possess the inhibitory activity.

DISCLOSURE OF THE INVENTION

The present invention is related to:

1) A heterocyclic (pyrrolidine derivative or thiazolidine derivative) compound of the general formula:

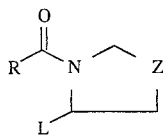 (I)

wherein, Z represents methylene group or sulfur atom,
R represents the general formula:

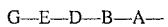

wherein, A represents a bond, alkylene group of from 1 to 6 carbon atom(s), alkenylene group of from 2 to 6 carbon atoms, a group of the general formula:

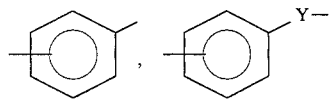

wherein, Y represents alkylene group of from 1 to 4 carbon atom(s) or alkenylene group of from 2 to 4 carton atoms or a saturated hydrocarbon ring of from 4 to 7 carbon atoms or heterocyclic mono ring. B represents a bond or alkylene group of from 1 to 6 carbon atom(s). D represents a bond, oxygen atom, carbonyl group or a group of the general formula:

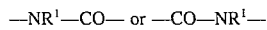

wherein, $R^1$ represents hydrogen atom, alkyl group of from 1 to 6 carbon atom(s), phenyl group or benzyl group.

E represents a bond, alkylene group of from 1 to 8 carbon atom(s) or alkylene group of from 1 to 8 carbon atom(s) substituted by phenyl or benzyl group.

G represents a carbocyclic or heterocyclic ring which is unsubstituted or substituted by 1~3 of alkyl group of from 1 to 6 carbon atom(s), alkoxy group of from 1 to 6 carbon atom(s), halogen atom, trifluoromethyl group or nitro group.

L represents a group of the general formula:

$-CO-COR^2$
$-CH(OH)-COR^2$
$-CH(OR^3)_2$

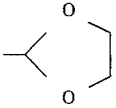

$-CH(OH)-R^4$
$-CO-R^4$
$-CO-CH_2-COR^2$
$-CH(OH)-CH_2-COR^2$
$-CO-CF_2-COR^2$
$-CH(OH)-CF_2-COR^2$
$-CO-CO-NR^5R^6$
or
$-CO-CH_2-CO-NR^5R^6$ wherein, $R^2$ represents hydrogen atom, hydroxy group, alkyl group of from 1 to 6 carbon atom(s), alkoxy group of from 1 to 6 carbon atom(s), phenyl group, alkyl group of from 1 to 6 carbon atom(s) substituted by phenyl group or alkoxy group of from 1 to 6 carbon atom(s) substituted by phenyl group.

$R^3$ represents alkyl group of from 1 to 6 carbon atom(s), phenyl group, or alkyl group of from 1 to 6 carbon atom(s) substituted by phenyl group.

$R^4$ represents alkyl group of from 1 to 6 carbon atom(s), phenyl group, alkyl group of from 1 to 6 carbon atom(s) substituted by phenyl group or trifluoromethyl group.

$R^5$ and $R^6$ independently represents hydrogen atom, alkyl group of from 1 to 6 carbon atom(s), phenyl group, or alkyl group of from 1 to 6 carbon atom(s) substituted by phenyl group.

With the proviso that the following compounds are excluded:
(i) Compounds wherein both of A and B are bonds.
(ii) Compounds wherein Z is methylene group, and t is a group of general formula:

$-CO-COR^2$
$-CH(OH)-COR^2$
$-CH(OR^3)_2$

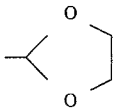

or
$-CH(OH)-R^4$ wherein all of the symbols are the same meaning as in hereinbefore defined.
and
R is
(1) a group of general formula:

G'—E—CONH—B—A—

(2) a group of general formula:

G'—CO—B—A—

(3) a group of general formula:

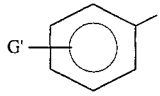

(4) a group of general formula:

G'—O—Alk—

(5) a group of general formula:

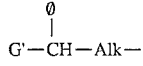

(6) a group of general formula:

G'—Alk—

(7) a group of general formula:

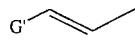

(8) a group of general formula:

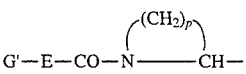

wherein, G' represents benzene ring which is unsubstituted or substituted by substituent(s).
Alk represents a bond or alkylene group of from 1 to 3 carbon atom(s).
p represents an integer of from 1~5 and non-toxic salts or hydrate thereof 2) Processes for the preparation of them; and
3) Anti-amnesia agents containing them as an active ingredient.

The following groups of compounds are included in the present invention, that is:

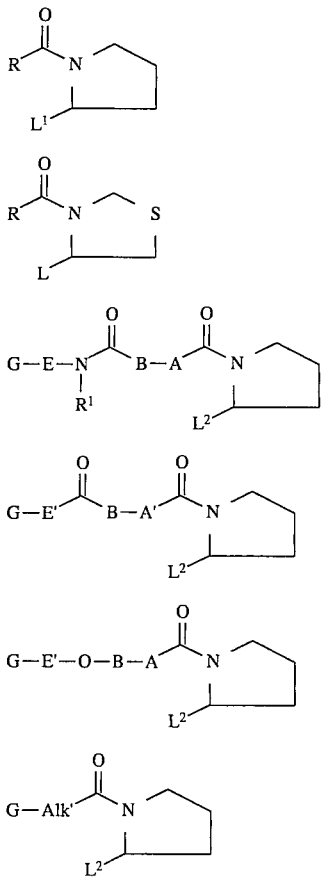

wherein, $L^1$ represents a group of the general formula:

—CO—$R^4$

—CO—$CH_2$—$COR^2$

—CH(OH)—$COR^2$

—CO—$CF_2$—$COR^2$

—CH(OH)—$CF_2$—$COR^2$

—CO—CO—$NR^5R^6$ or

—CO—$CH_2$—CO—$NR^5R^6$ wherein all of the symbols are the same meaning as hereinbefore defined.

$L^2$ represents a group of the general formula:

—CO—$COR^2$
—CH(OH)—$COR^2$
—CH($OR^3$)$_2$

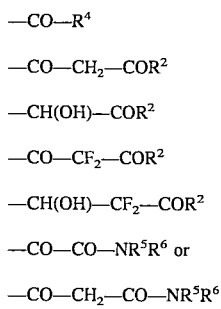

or
—CH(OH)—$R^4$ wherein all of the symbols are the same meaning as hereinbefore defined.

A' represents a bond, alkylene group of from 1 to 6 carbon atom(s), alkenylene group of from 2 to 6 carbon atom(s), or a group of the general formula:

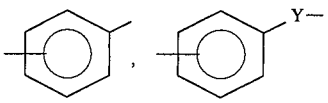

wherein, Y represents alkylene group of from 1 to 4 carbon atom(s) or alkenylene group of from 2 to 4 carbon atoms.
a saturated hydrocarbon ring of from 4 to 7 carbon atoms or heterocyclic mono ring containing two hetero atoms.

E' represents alkylene group of from 1 to 8 carbon atom(s), alkylene group of from 1 to 8 carbon atom(s) substituted by phenyl or benzyl group.

Alk' represents alkylene group of from 4 to 20 carbon atoms.

In the general formula (I) and (Id), "alkylene group of from 1 to 6 carbon atom(s)" represented by A, A' and B means methylene, ethylene, trimethylene, tetramethylene, pentamethylene and hexamethylene groups and isomers thereof.

In the general formula (I), (Id) and (Ie), "alkylene group from 1 to 8 carbon atom(s)" represented by E and E' means groups described above including heptamethylene and octamethylene groups and isomers thereof.

In the general formula (I), "alkylene group of from 1 to 4 carbon atom(s)" represented by Y means methylene, ethylene, trimethylene and tetramethylene group and isomers thereof.

In the general formula (I), "alkenylene group of from 2 to 4 carbon atoms" represented by Y means vinylene, propenylene, butenylene and butadienylene groups and isomers thereof.

In the general formula (I) and (Id), "alkenylene group of from 2 to 6 carbon atoms" represented by A and A' means groups described above including pentenylene, pentadienylene, hexenylene, hexadienylene and hexatrienylene groups and isomers thereof.

In the general formula (I) and (Id), "saturated hydrocarbon ring of from 4 to 7 carbon atoms" represented by A and A' means cyclobutane, cyclopentane, cyclohexane and cycloheptane.

In the general formula (I), heterocyclic mono ring represented by A means aromatic rings of from 3 to 7 ring members and wherein 1 or 2 hetero atom(s), which may be partially or fully saturated.

Examples of the rings mentioned above are furan, thiophene, pyrrole, oxazole, isoxazole, thiazole, isothiazole, imidazole, pyrazole, furazane, pyran, pyridine, pyridazine, pyrimidine, pyrazine rings and partially or fully saturated rings thereof.

In the general formula (I), preferred heterocyclic rings represented by A especially are piperidine, pyrrolidine and thiazolidine rings.

In the general formula (Id), heterocyclic mono ring containing two hetero atoms means aromatic rings containing from 3 to 7 ring members which may be partially or fully saturated.

Examples of the rings mentioned above are oxazole, isoxazole, thiazole, isothiazole, imidazole, pyrazole, furazone, pyridazine, pyrimidine, pyrazine rings and partially or fully saturated rings thereof.

In the general formula (I), preferred heterocyclic ring represented by A' especially is thiazolidine ring.

In the general formula (If), "alkylene group of from 4 to 20 carbon atoms" represented by Alk' means tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, eicosamethylene groups and isomers thereof.

In the general formula (I), "alkylene group of from 1 to 3 carbon atom(s)" represented by Alk means methylene, ethylene, trimethylene group and isomers thereof.

In the general formula (I) "alkyl group of from 1 to 6 carbon atom(s)" represented by $R^1$, $R^2$, $R^3$, $R^4$, $R^5$ and $R^6$ means methyl, ethyl, propyl, butyl, pentyl and hexyl groups and isomers thereof.

In the general formula (I), "alkyl group of from 1 to 6 carbon atom(s)" in G and G' means the same as above.

In the general formula (I), "alkoxy group of from 1 to 6 carbon atom(s)" in $R^2$, G and G' means methoxy, ethoxy, propoxy, butoxy, penthyloxy and hexyloxy groups and isomers thereof.

In the general formula (I), "halogen atom" in G and G' means chlorine, bromine, fluorine and iodine atoms.

In the general formula (I), "carbocyclic ring" represented by G means mono-, di- or tri-cyclic aromatic carbocyclic ring(s) containing not more than 15 carbon atoms which may be partially or fully saturated.

Examples of the rings mentioned above are benzene, naphthalene, indene, azulene, fluorene, phenanthrene, anthracene, acenaphthalene, biphenylene rings and partially or fully saturated rings thereof.

In the general formula (I), "heterocyclic ring" represented by G means mono-, di- or tri-aromatic heterocyclic ring(s) containing not more than 15 carbon and hetero atoms which may be partially or fully saturated. In above heterocyclic rings, rings containing one or two of hetero atom(s) are preferred.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinoxaline, phthalazine, pteridine, carbazole, acridine, phenanthridine, xanthene, phenazine, phenothiazine rings and partially or fully saturated rings thereof.

In the general formula (I), preferred ring represented by G especially are benzene, naphthalene, fluorene, pyridine, furan, isoquinoline and acridine rings and partially saturated rings thereof.

In the above rings, substituted benzene rings are preferred as substituted rings by substituent(s).

In the present invention, hetetro atom(s) in the heterocyclic ring(s) means nitrogen, oxygen and sulfur atoms.

Throughout the specification including the claims, stereo isomers generated by stereo configuration(s) (asymmetric carbon, double bond etc.) and structural isomers generated by branching of a carbon chain, etc., are included in the present invention.

For example, it may be easily understood that alkylene and alkenylene groups include straight-chained and also branched-chained ones, to the skilled in the art.

Rings represented by A or rings in G may be attached to the adjacent group at any position.

NON-TOXIC SALTS

Among the compounds of the present invention of the general formula (I), compounds wherein L contains carboxy group may be converted into the corresponding salts. Non-toxic and water-soluble salts are preferable. Suitable salts, for example, are the following: salts of alkaline metals (sodium, potassium, etc.), salts of alkaline earth metals (calcium, magnesium, etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.). The, the present invention also includes hydrate.

Process for the preparation of the compounds of the present invention (1)

Among the compounds of the present invention of the general formula (I), compounds of the general formula:

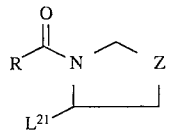
(IA)

wherein, $L^{21}$ represents a group of general formula:

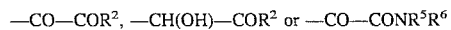

wherein, all of the symbols have the same meaning as hereinbefore described, and the other symbols are the same meaning as hereinbefore defined,
may be prepared by processes described in the following reaction scheme [A].
Symbols in each formula represent the following meaning or as hereinbefore defined.
$R^{21}$: alkoxy group of from 1 to 6 carbon atom(s)

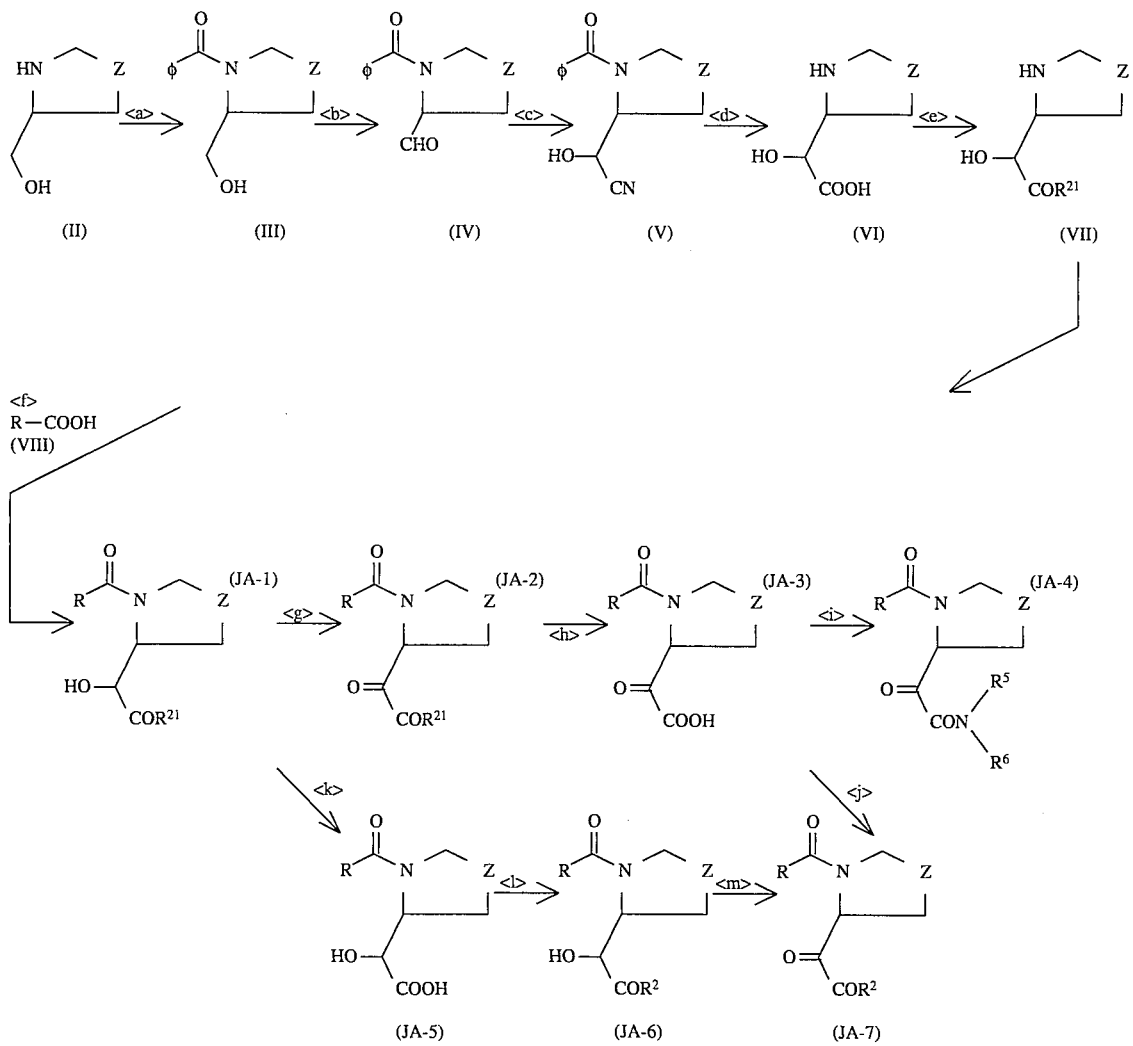

Scheme [A]

All of the reactions in the scheme [A] are known reactions; brief descriptions are the following:

Step <a> is N-acylation, and it may be carried out, for example, using benzoyl chloride and an aqueous solution of alkali (sodium bicarbonate, etc.) in a water-miscible organic solivent (acetone, etc.).

Step <b> is oxidation, and it may be carried out, for example, by method of Swern oxidation or Jones' oxidation.

Step <c> is hydrocyanation, and it may be carried out, for example, using sodium cyanate, in the presence of an acid (hydrochloric acid, etc.), in a water-miscible organic solvent (THF, etc.).

Step <d> is hydrolysis, and it may be carried out, for example, by refluxing in the presence of an acid (hydrochloric acid, etc.).

Step <e> is esterification, and it may be carried out; for example, using thionyl chloride or hydrochloride gas in a corresponding alcohol (methanol, ethanol, etc.)

Step <f> is a reaction to form amide, and it may be carried out, for example, to convert a carboxylic acid of the general formula (VIII) into a corresponding acid halide using an acid halogenating-agent (thionyl chloride, oxalyl chloride, etc.), and the acid halide obtained was reacted with an amine of the general formula (VII) in the presence of a tertiary amine (triethylamine, etc.) in an inert organic solvent (methylene chloride etc.); or to convert a carboxylic acid of the general formula (VIII) into an activated ester using a mixed acid anhydride (isobutyl chloroformate, ethylchloroformate, pivaloyl chloroformate, etc.). and the ester obtained was reacted with an amine of the general formula (VII) in the presence or absence of a tertiary amine (same as above).

Step <g> is oxidation, and it may be carried out, for example, by the method of Swern oxidation or Jones' oxidation.

Step <h> is hydrolysis, and it may be carried out, for example, using an aqueous solution of alkali (potassium carbonate, sodium hydroxide, etc.) in a water-miscible organic solvent (methanol, etc.).

Step <i> is a reaction to form amide, and it may be carried out, for example, using a chloroformic acid ester (isobutyl chloroformate, etc.) and a corresponding amine in the presence of a tertiary amine.

Step <j> is esterification, and it may be carried out, for example, using a halogenating agent (benzyl bromide, alkyl bromides etc.), in the presence of a base (potassium carbonate, triethylamine, etc.), in an inert organic solvent (DMSO, DMF, acetone, etc.).

Step <k> is hydrolysis, and it may be carried out by the procedure as described in step <h>.

Step <l> is esterification, and it may be carried out by the same procedure as described in step <J>.

Step <m> is oxidation, and it may be carried out by the same procedure as described in step <g>.

Process for the preparation of the compounds of the present invention (2)

Among the compounds of the present invention of the general formula (I), compounds of general formula:

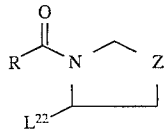
(IB)

wherein, $L^{22}$ represents

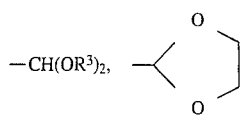

$-CH(OH)-R^4$,  $-CO-R^4$,  $-CO-CH_2-COR^2$,
$-CH(OH)-CH_2-COR^2$,  $-CO-CF_2-COR^2$,
$-CH(OH)-CF_2-COR^2$  or
$-CO-CH_2-CO-NR^5R^6$,  and the other symbols are the same meaning as hereinbefore defined, may be prepared by processes described in the following reaction scheme [B] or [C].

Symbols in each formula represents the following meaning or are as hereinbefore defined.

$R^{41}$: alkyl group of from 1 to 6 carbon atom(s), phenyl group, or alkyl group substituted by phenyl group.

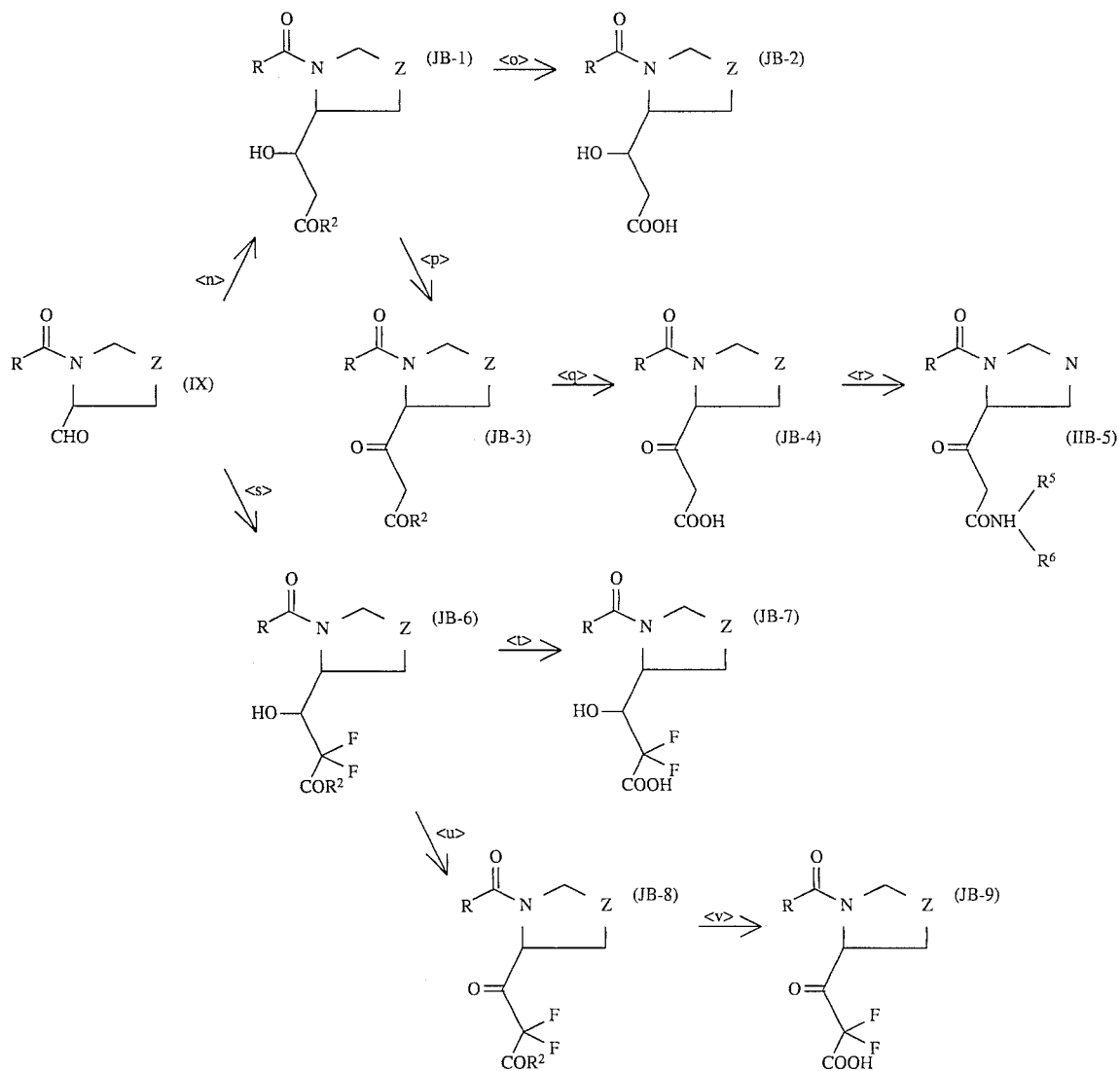

Scheme [B]

Scheme [C]

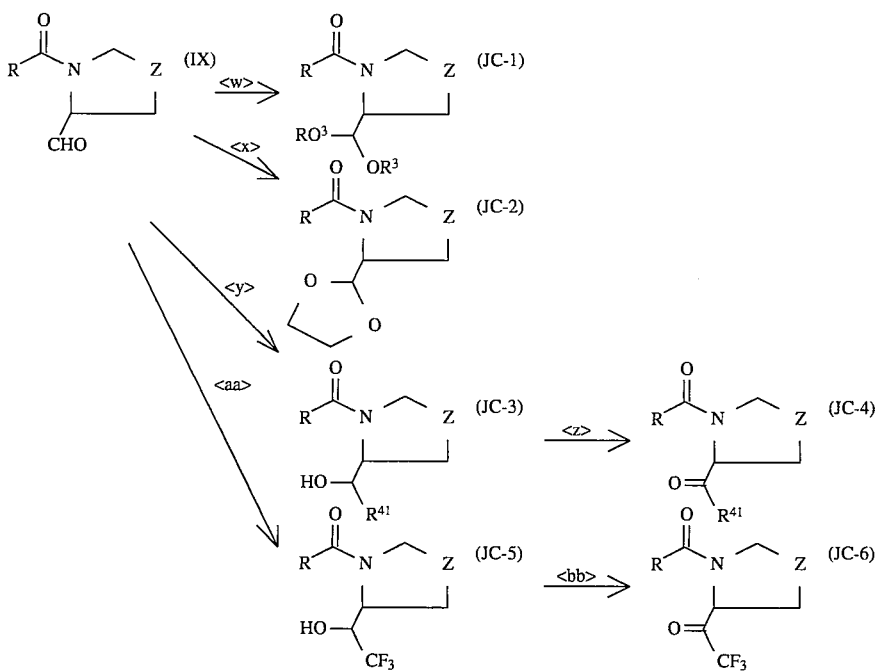

All of the reactions in scheme [B] and [C] are known reactions and brief descriptions are the following:

Step <n> is Reformatskij reaction, and it may be carried out, for example, by refluxing with a corresponding alkyl bromoacetate, in the presence of zinc powder and iodine, in an inert organic solvent (THF, benzene etc.).

Step <o> is hydrolysis, and it may be carried out by the same procedure as discribed in step <h>.

Step <p> is mild-oxidation, and it may be carried out, for example, using Dess-Martin reagent, in an inert organic solvent (methylene chloride, etc.).

Step <q> is hydrolysis, and it may be carried out by the same procedure as described in step <h>.

Step <r> is a reaction to form amide, and it may be carried out by the same procedure as described in step <i>.

Step <s> is Reformatskij reaction and it may be carried out by the same procedure as described instep <n>, using a corresponding alkyl bromodifluoroacetate in stead of alkyl bromoacetate.

Step <t> is hydrolysis, and it may be carried out by the same procedure as described in step <h>.

Step <u> is mild-oxidation, and it may be carried out by the same procedure as described in step <p>.

Step <v> is a hydrolysis, and it may be carried out by the same procedure as described in step <h>.

Step <w> is a reaction to form acetal, and it may be carried out, for example, using acid, catalyst (camphorsulphonic acid, p-toluenesulphonic acid etc.) in an alcohol (methanol, ethanol, etc.).

Step <x> is a reaction to form acetal, and it may be carried out, for example, by refluxing with ethylene glycol, in the presence of an acid catalyst (p-toluenesulphonic acid etc.), in an inert organic solvent (benzene, etc.).

Step <y> is Grignard reaction, and it may be carried out, for example, using a corresponding Grignard reagent (alkylmagnesium chloride, etc.) in an ether (THF etc.).

Step <Z> is oxidation, and it may be carried out by the same procedure as described in step <g>.

Step <aa> is fluoroalkylation, and it may be carried out, for example, using trifluoromethyl iodide under the irradiation of ultrasonic waves.

Step <bb> is oxidation, and it may be carried out by the same procedure as described is step <u>.

Starting materials and reagents in the present invention are known per se. For example, the compounds of the general formula (VIII) and (IX) are described with processes for the preparation in European Patent Publication No. 268190, 277588 or 280956 or Japanese Patent Publication No. 63-162672 or 63-264454.

Throughout the specification, in each reactions, products may be purified by conventional methods, for example, distillation at atmospheric or reduced pressure, high performance liquid chromatography, thin layer chromatography using silica gel or magnesium silicate or washing or recrystallization. Purification may be carried out after each reaction or a series of reaction.

PHARMACOLOGICAL ACTIVITIES

The compounds of the present invention of the general formula (I) possess an inhibitory activity on prolyl endopeptidase, as described before. For example, in a standard laboratory test, results in the following were given.

Prolyl endopeptidase inhibitory activity in vitro

The compounds of the present invention showed activites as in the following Table I, with the test system described hereafter.

TABLE I

| Example No. of the compounds | Concentration for 50% inhibition $IC_{50}$ (μM) |
| --- | --- |
| 2 | 0.003 |
| 2 (b) | 0.0018 |
| 2 (d) | 0.00085 |

TABLE I-continued

| Example No. of the compounds | Concentration for 50% inhibition IC$_{50}$ (µM) |
| --- | --- |
| 2 (g) | 0.0017 |
| 2 (h) | 0.017 |
| 2 (l) | 0.0018 |
| 6 | 3.0 |
| 7 | 0.0012 |
| 9 | 0.023 |
| 12 | 69 |
| 13 | 0.10 |
| 15 | 1.5 |
| 15 (a) | 0.12 |
| 17 (a) | 0.18 |
| 19 | 14 |

Inhibitory activity of prolyl endopeptidase in vitro was measured by the following test system.

A mixed solution of 20 mM tris-HCl buffer (pH 7.5 : 935 µl; containing 10 mM EDTA and 10 mM mercaptoethanol), a solution of a compound of the present invention in DMSO (10 µl) and a solution of prolyl endopeptidase which was purified from bovine brain (0.13 unit ml; prepared by the method described in J. Biochem., 94, 1179 (1983) ) in tris-HCl buffer (15 µl) was preincubated for 15 mins at 37° C.

To the solution, 5 mM of N-benzyloxycarbonyl-glycyl-prolyl-p-nitroanilide (40 µl) in a mixture of 40% dioxane - 60% water was added. The solution was incubated for 1 min at the same temperature.

Optical absorption ($a_1$) at 405 nm of the solution, and optical absorption ($a_2$) at 405 nm of the solution after 30 mins' more incubation at 37° C. were measured.

Optical absorptions ($b_1$ and $b_2$) of the solutions using DMSO instead of the solution of the compound of the present invention were also measured.

Inhibitory ratio was calculated by the following expression and IC$_{50}$ (required concentration for 50% inhibition) was obtained (See Protein, Nucleic acid and Enzyme 25(6), 513, 1980.).

$$\text{Inhibitory ratio (\%)} = \frac{(b_2 - b_1) - (a_2 - a_1)}{b_2 - b_1} \times 100$$

TOXICITY

On the other hand, it was confirmed that the toxicity of the compounds of the present invention was very low. Therefore, the compounds of the present invention may be considered to be sufficiently safe and suitable for pharmaceutical use.

APPLICATION FOR PHARMACEUTICALS

To inhibit prolyl endopeptidase is to suppress the metabolism of neurotransmitters, substances taking part in memory in the brain (each of them is a peptide.) described hereinbefore, and therefore should be useful for prevention and/or treatment of amnesia, in animals including human beings, especially human beings.

The compounds of the present invention possess an inhibitory activity on prolyl endopeptidase in vitro, so they are expected to be useful for prevention and/or treatment of amnesia.

For the purpose above described, the compounds of the present invention may normally by administered systemically or locally, usually by oral or parenteral administration.

The doses to be administered are determined depending upon age, body weight, symptom, the desired therapeutic effect, the route of administration, and the duration of the treatment, etc. In the human adult, the doses per person per dose are generally between 1 mg and 500 mg, by oral administration, up to several times per day, and between 1 mg and 100 mg, by parenteral administration (preferably, intravenous administration) up to several times per day.

As mentioned above, the doses to be used depend upon various conditions. Therefore, there are cases in which doses lower than or greater than the ranges specified above may be used.

At the administration, the compounds of the present invention may be formed into solid compositions, liquid compositions or the other compositions for oral administration, injection compositions, external compositions, suppositories, etc., for parenteral administration.

Solid compositions for oral administration include compressed tablets, pills, capsules, dispersible powders; and granules. In such solid compositions one or more of the active compound(s) is or are, admixed with at least one inert diluent (lactose, mannitol, glucose, hydroxypropylcellulose, micrycrystalline cellulose, starch, polyvinylpyrrolidone, magnesium metasilicate aluminate, etc.). The compositions may also comprise, as is normal practice, additional substances other than inert diluents: e.g., lubricating agents (magnesium stearate etc.), disintegrating agents (cellulose calcium gluconate, etc.), assisting agents for dissolving (glutamic acid, aspartic acid, etc.) stabilizing and agents (lactose, etc.).

The tablets or pills may, if desired, be coated with a film of gastric or enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable solutions, emulsions, suspensions, syrups and elixirs.

In such liquid compositions, one or more of the active compound(s) is or are used in inert diluent(s) commonly used in the art (purified water, ethanol, etc.).

Besides inert diluents, such compositions may also comprise adjuvants (wetting agents, suspending agents, etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g., stabilizing agents (sodium sulfite, etc.), isotonic buffer (sodium chloride, sodium citrate, citric acid, etc.).

For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one or more of active compound(s) is or are admixed with at least one of inert aqueous diluent(s) (distilled water for injection, physiological salt solution, etc.) or inert non-aqueous diluent(s) (propylene glycol, polyethylene glycol, olive oil, ethanol, POLYSORBATE 80 (registered trade mark) etc.).

Injections may comprise other than inert diluents: e.g., preserving agents, wetting agents, emulsifying agents, dispersing agents, stabilizing agents (lactose, etc.), assisting agents such as assisting agents for dissolving (glutamic acid, aspartic acid, etc.).

They may be sterilized, for example, by filtration through a bacteria-retaining filter, by incorporation of sterilizing agents in the compositions or by irradiation. They may also be manufactured in the form of sterile solid compositions, for example, by freeze-drying, which can be dissolved in sterile water or some other sterile diluents for injection immediately before use.

Other compositions for parenteral administration include liquids for external use, and endermic liniments (ointments, etc.), suppositories and pessaries which comprise one or more of the active compound(s) and which may be prepared by known methods.

REFERENCE EXAMPLES AND EXAMPLES

The following reference examples and examples are to illustrate the present invention, but not limit the present invention.

The solvents in the parentheses show the developing or eluting solvents and the ratios of the solvents used are by volume in chromatographic separations.

Unless otherwise specified, "IR" were measured by a liquid film method.

REFERENCE EXAMPLE 1

Synthesis of (2S)-1-benzoylpyrrolidine-2-methanol

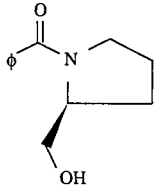

Benzoyl chloride (18.5 ml) and an aqueous (50 ml) solution of sodium carbonate (17.0 g) were added dropwise to a solution of (S)-2-pyrrolidinemethanol (12.0 g) in a mixture of acetone (70 ml) and water (14 ml). After addition, the reaction mixture was stirred for 30 mins at room temperature. The reaction mixture was filtered. Water was added to the filtrate. The mixture was extracted with methylene chloride. The extract was washed, dried and evaporated. The residue was purified by column chromatography on silica-gel (hexane-EtOAc) to give the title compound (24.1 g) having the following physical data:
TLC: Rf 0.19 (EtOAc).

REFERENCE EXAMPLE 2

Synthesis of (2S)-1-benzoylpyrrolidin-2-al

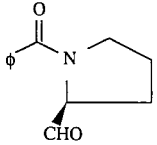

A solution of DMSO (27.9 ml) in methylene chloride (50 ml) was added to a solution of oxalyl chloride (16.4 ml) in methylene chloride (300 ml) which was cooled to −70° C. A solution of (2S)-1-benzoylpyrrolidine-2-methanol (24.1 g) in methylene chloride (120 ml) was added dropiwise to the solution at −70° C. The mixture was stirred for 30 mins. Triethylamine (89.5 ml) was added dropwise to the reaction solution at −70° C. The mixture was stirred for 50 mins at the same temperature, and then rised to 0° C. gradually. Water was added to the solution.

The mixture was extracted with methylene chloride. The extract was washed, dried, and evaporated. The residue was purified by column chromatography on silica gel (hexane-EtOAc) to give the title compound (23.7 g) having the following physical data:
TLC: RF 0.38 (EtOAc)

REFERENCE EXAMPLE 3

Synthesis of (2RS)-2-t(2S)-1-benzoylpyrrolidine)-2-hydroxyacetonitrile

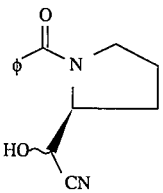

(2S)-1-benzoylpyrrolidin-2-al (23.7 g) was dissolved into a mixture of THF (200 ml) and water (135 ml). Sodium cyanate (8.36 g) was added to the solution.

Conc. hydrochloric acid (10 ml) was added to the mixture with ice-cooling. The reaction mixture was stirred for 1 hr. at the same temperature, and for 20 mins. at room temperature. Water was added to the reaction mixture. The mixture was extracted with methylene chloride. The extract was washed, dried and evaporated to give the title compound having the following physical data:
TLC: Rf 0.44 & 0.51 (EtOAc)

REFERENCE EXAMPLE 4

Synthesis of (2RS)-2-[(2S)-pyrrolidin-2-yl]-2-hydroxyacetic acid

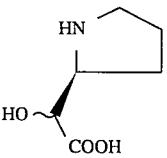

Conc. hydrochloric acid (210 ml) was added to (2RS)-2-[(2S)-1-benzoylpyrrolidine)- 2-hydroxyacetonitrile (21 mg). The mixture was refluxed for 1 hr.

The reaction solution was cooled to room temperature, and filtered. The filtrate was diluted with water. The solution was washed with ether. The water layer was absorbed onto an amberite column. The column was eluted with aqueous ammonia.

The eluented solution was evaporated. The concentrate was dissolved in water. The solution was treated with active carbon. The filtrate was evaporated. The residue was cooled to −10° C. to deposit crystals. The crystals were gathered to give the title compound (5.84 g) having the following physical data:

TLC: Rf 0.16 (EtOAc: AcOH: H₂O=3:1: 1)

REFERENCE EXAMPLE 5

Synthesis of (2S)-1-[3-(N-benzyl-N-methylcarbamoyl) propanoyl]pyrrolidine-2-methanol

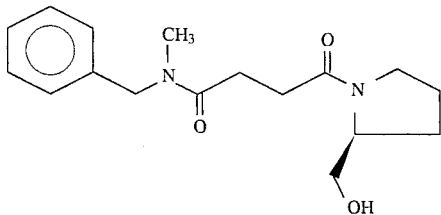

Triethylamine (4.0 ml) and isobutyl chloroformate (1.86 ml) were added dropwise to a solution of 3-(N-benzyl-N-methylcarbamoyl) propionic acid (2.5 g) in THF (30 ml) cooled to −20° C. The mixture was stirred for 30 mins at the same temperature. Triethylamine (4 ml) was added to a solution of (S)-2-pyrrolidinemethanol (1.45 g) in THF (30 ml). To the solution cooled to −25° C., the above solution was added dropwise.

The mixture was stirred for 1 hr at the same temperature. After reaction, water was added to the reaction solution. The mixture was extracted with EtOAc. The extract was washed, dried and evaporated. The residue was purified by column chromatography on silica gel (CH₂Cl₂—CH₃OH) to give the title compound (2.59 g) having the following physical data:

TLC: Rf 0.24 (EtOAc: CH₃OH=9:1)

REFERENCE EXAMPLE 6

Synthesis of (2S)-1-( 3-(N-benzyl-N-methylcarbamoyl) propanoyl)pyrrolidin-2-al]

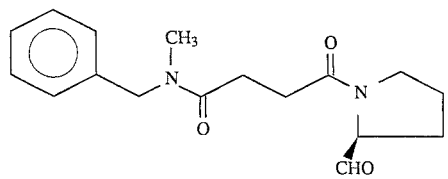

By the same procedure described in reference example 2, using (2S)-1-[3-(N-benzyl-N-methylcarbamoyl)propanoyl)pyrrolidine-2-methanol (2.59 g), the title compound (2.37 g) having the following physical data. was given:

TLC : Rf 0.40 (EtOAc: CH₃OH=9:1)

EXAMPLE 1

Synthesis of (2RS)-2-[(2S)-1-[3-(N-benzyl-N-methylcarbamoyl) propanoyl]pyrrolidin-2-yl )-2-hydroxyacetic acid ethyl ester

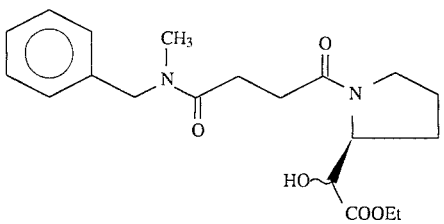

Triethylamine (3.5 ml) and isobutyl chloroformate (980 μl) were added to a solution of 3-(N-methyl-N-benzylcarbamoyl) propionic acid (1.33 g) in THF (16 ml). The mixture was stirred for 15 mins at −15° C. The solution was named solution Ⓐ. (2RS)-2-[(2S)-pyrrolidin-2-yl)- 2-hydroxyacetic acid (1.0 g) was dissolved in ethanol (25 ml). The solution was cooled to −20° C. Thionyl chloride (1.0 ml) was added dropwise to the cooled solution. The mixture was stirred for 2 hrs. at room temperature. Triethylamine (5 ml) was added dropwise to the solution cooled to −20° C. again. The solution was allowed to stand to rise to room temperature, and evaporated.

THF (26 ml) and triethylamine (1.15 ml) were added to the residue. To the solution cooled to −10° C., the above solution Ⓐ was added dropwise. The mixture was stirred for 2 hrs at room temperature. Water was added to the reaction solution. The mixture was extracted with EtOAc. The extract was washed, dried and evaporated. The residue was purified by column chromatography on silica gel (hexane - EtOAc) to give the title compound (1.67 g) having the following physical data:

TLC: Rf 0.41 (CH₂Cl₂:CH₃OH=9:1);

IR (CHCl₃ solution):

ν 3470~3350, 3000, 1730, 1630, 1440, 1250~1210, 1120 cm⁻¹.

EXAMPLE 1 (a)–1 (n)

By the same procedure as is described in title compounds having the physical data shown in table II were given.

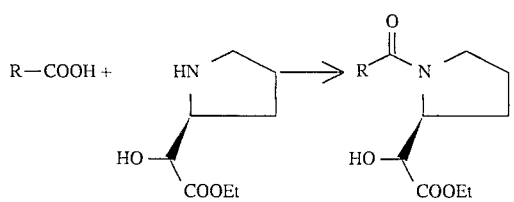

TABLE II

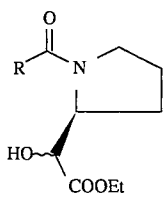

| Example No. | R— | Name | TLC | IR (vcm⁻¹) |
|---|---|---|---|---|
| 1 (a) | φ-(CH₂)₉— | 2-[(2S)-1-(10-phenyldecanoyl) pyrrolidin-2-yl]-2-hydroxyacetic acid ethyl ester | Ref 0.34 (hexane:EtOAc = 1:1) | 3450~3200, 2900, 2840, 1720, 1630, 1610, 1430, 1250, 1180, 1100 |
| 1 (b) | (4-CF₃-phenyl-CH₂-N(Ph)-CO-CH₂CH₂-) | 2-[(2S)-1-[3-[N-4-trifluoromethylphenylmethyl)-N-phenylcarbamoyl]propanoyl]pyrrolidin-2-yl]-2-hydroxyacetic acid ethyl ester | Ref 0.14 (hexane:EtOAc = 1:1) | 3450~3300, 2950, 1720, 1650~1610, 1590, 1490, 1420, 1390, 1315, 1260, 1110, 1060, 1010, 690 |
| 1 (c) | φ-(CH₂)₄-O-(4-phenyl)-CH=CH- | 2-[(2S)-1-[3-[4-(4-phenylbutoxy)phenyl]propenoyl]pyrrolidin-2-yl]-2-hydroxyacetic acid ethyl ester | Rf 0.26 (hexane:EtOAc = 1:1) | 2950, 1720, 1630, 1580, 1500, 1410, 1240, 1160, 820, 690 |
| 1 (d) | (4-Cl-phenyl-CH₂-NH-CO-CH₂CH₂-) | 2-[(2)-1-[3-[N-(4-chlorophenylmethyl)carbamoyl]propanoyl]pyrrolidin-2-yl]-2-hydroxyacetic acid etyl eter | Rf 0.31 (CH₂Cl₂:CH₃OH = 10:1) | 3300, 2990~2930, 1730, 1630, 1610, 1550~1530, 1490, 1440~1430, 1240, 1200, 1095, 1015 |
| 1 (e) | (9-fluorenyl-NH-CO-CH₂CH₂-) | 2-[(2S)-1-[3-[N-(9-fluorenyl)carbamoyl]propanoyl]pyrrolidin-2-yl]-2-hydroxyacetic acid ethyl ester | Rf 0.42 (CH₂Cl₂:CH₃OH = 10:1) | 3460, 2990, 1725, 1655, 1630, 1500, 1445, 1370, 1245~1205, 1115 |
| 1 (f) | φ-(CH₂)₅-CH(iPr)- | 2-[(2S)-1-[(2RS)-2-isopropyl-7-phenylheptanoyl]pyrrolidin-2-yl]-2-hydroxyacetic acid ethyl ester | Rf 0.67 (hexane:EtOAc = 1:1) | 3350, 1720, 1600, 1420, 1100, 1020, 740, 690 |
| 1 (g) | (1-naphthyl-CH₂-N(CH₃)-CO-CH₂CH₂-) | 2-[(2S)-1-[3-[N-(1-naphthyl)methyl-N-methylcarbamoyl]propanoyl]pyrrolidin-2-yl]-2-hydroxyacetic acid ethyl ester | Rf 0.33 (EtOAc:CH₃OH = 19:1) | 3350, 1720, 1620, 1400, 1100, 790, 670 |
| 1 (h) | (φ-CH₂CH₂-CO-cyclopentyl-) | 2-[(2S)-1-[(1RS,2R)-2-(3-phenylpropanoyl)cyclopentanecarbonyl]pyrrolidin-2-yl]-2-hydroxyacetic acid ethyl ester | Rf 0.56 (EtOAc:hexane = 2:1) | 3400, 1690, 1610, 1420, 1180, 1090, 1010, 740, 670 |
| 1 (i) | (φ-CH₂-NH-CO-cyclopentyl-) | 2-[(2S)-1-[(1RS,2R)-2-(N-benxylcarbamoyl)cyclopentanecarbonyl]pyrrolidin-2-yl]-2-hydroxyacetic acid ethyl ester | Rf 0.20 (EtOAc:hexane = 2:1) | 3300, 1720, 1600, 1510, 1420, 1220, 1090, 1010, 670 |

TABLE II-continued

[Structure: R-C(=O)-N-pyrrolidine with HO and COOEt substituents at 2-position]

| Example No. | R— | Name | TLC | IR (vcm⁻¹) |
|---|---|---|---|---|
| 1 (j) | [2,4-dichlorobenzyl-NH-C(=O)-CH₂CH₂-] | 2-[(2S)-1-[3-[N-(2,4-dichlorophenylmethyl)carbamoyl]propanoyl]pyrrolidin-2-yl]-2-hydroxyacetic acid ethyl ester | Rf 0.35 (EtOAc:CH₃OH = 19:1) | 3300, 3050, 1710, 1600, 1520, 1410, 1240, 1180, 1090, 1010, 810, 665 |
| 1 (k) | [4-methoxyphenyl-(CH₂)₄-CH(iPr)-] | 2-[(2S)-1-[(2RS)-2-isopropyl-6-(4-methoxyphenyl)hexanoyl]pyrrolidin-2-yl]-2-hydroxyacetic acid ethyl ester | Rf 0.31 (hexane:EtOAc = 2:1) | 3300, 1720, 1600, 1500, 1420, 1240, 1100, 1020, 810, 670 |
| 1 (l) | [φ-CH₂-N(t-Bu)-C(=O)-CH₂CH₂-] | 2-[(2S)-1-[3-(N-benzyl-N-t-butylcarbamoyl)propanoyl]pyrrolidin-2-yl]-2-hydroxyacetic acid ethyl ester | Rf 0.49 (CH₂Cl₂:CH₃OH = 10:1) | 3480–3370, 2975, 1735, 1640–1620, 1410, 1360, 1190, 1110, 1025, 750, 710 |
| 1 (m) | [φ-N(CH₂φ)-C(=O)-CH₂CH₂-] | 2-[(2S)-1-[3-(N-benzyl-N-phenylcarbamoyl)propanoyl]pyrrolidin-2-yl]-2-hydroxyacetic acid ethyl ester | Rf 0.48 (CH₂Cl₂:CH₃OH = 10:1) | 3450–3350, 2980, 1735, 1635, 1595, 1495, 1405, 1265, 1200, 1025, 780, 730, 700 |
| 1 (n) | [φ-CH₂CH₂-C(=O)-CH₂CH₂CH₂-] | 2-[(2S)-1-(4-oxo-7-phenylheptanoyl)pyrrolidin-2-yl]-2-hydroxyacetic acid ethyl ester | Rf 0.29 (EtOAc:hexane = 2:1) | 3400, 1700, 1610, 1410, 1090, 1010, 740, 670 |

EXAMPLE 2

Synthesis of 2-[(2S)-1-[3-(N-benzyl-N-methylcarbamoyl)propanoyl]pyrrolidin-2-yl]-2-oxoacetic acid ethyl ester

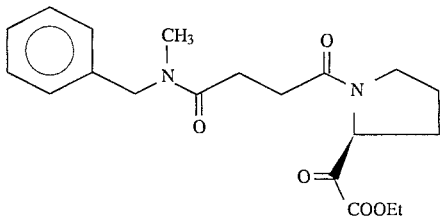

DMSO (443 μl) was added dropwise to a solution of oxyalyl chloride (260 μl) in methylene chloride (10 ml) cooled to −78° C. The solution was stirred for 15 mins at the same temperature. A solution of (2RS)-2-((2S)-1-[3-(N-benzyl-N-methylcarbamoyl)propanoyl)pyrrolidin-2-yl]-2-hydroxyacetic acid ethyl ester (700 mg) in methylene chloride (6 ml) was added dropwise to the solution at the same temperature. The mixture was stirred for 20 mins. Triethylamine (1.42 ml) was added dropwise to the solution. The solution was stirred for 10 mins at the same temperature, and for 30 mins. at 0° C.

Water was added to the reaction solution. The mixture was extracted with EtOAc. The extract was washed, dried and evaporated. The residue was purified by column chromatography on silica gel (hexane - EtOAc) to give the title compound (627 mg) having the following physical data:

TLC: Rf 0.18 (EtOAc);

IR (CHCl₃ solution):

ν 3000, 1725, 1630, 1440, 1205, 1050 cm⁻¹

EXAMPLE 2(a)–2(s)

By the same procedure as is described in example 2, title compounds having the physical data shown in table III were given.

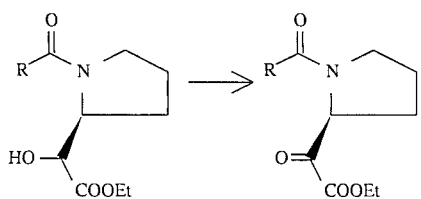

TABLE III

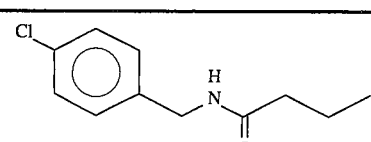

| Example No. | R— | Name | TLC | IR (νcm⁻¹) or mp |
|---|---|---|---|---|
| 2 (a) | 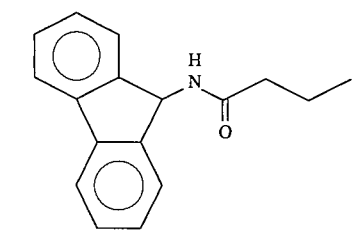 | 2-[(2S)-1-[3-[N-(4-chlorophenylmethyl)carbamoyl]propanoyl]pyrrolidin-2-yl]-2-oxoacetic acid ethyl ester | Rf 0.18 (EtOAc) | 3300, 3070, 2980, 1720, 1640,~1615, 1550~1525, 1490, 1435, 1370, 1260, 1130, 1090, 1055, 1010 |
| 2 (b) | 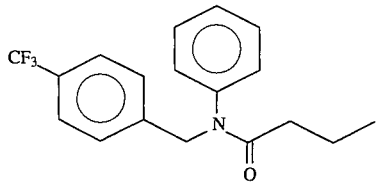 | 2-[(2S)-1-[3-[N-(9-fluorenyl)carbamoyl]propanoyl]pyrrolidin-2-yl]-2-oxoacetic acid ethyl ester | Rf 0.31 (EtOAc) | mp 142~146° C. |
| 2 (c) | φ-(CH$_2$)$_9$— | 2-[(2S)-1-(10-phenyldecanoyl)pyrrolidin-2-yl]-2-oxoacetic acid ethyl ester | Rf 0.48 (EtOAc:hexane = 1:1) | 3000~2800, 1740~1710, 1650~1610, 1430~1400, 1250, 1100, 1050, 740, 690 |
| 2 (d) | 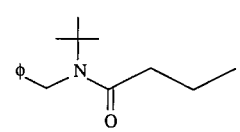 | 2-[(2S)-1-[3-[N-(4-trifluoromethylphenylmethyl)-N-phenylcarbamoyl]propanoyl]pyrrolidin-2-yl]-2-oxoacetic acid ethyl ester | Rf 0.14 (EtOAc:hexane = 1:1) | 3000~2350, 1740~1710, 1650~1600, 1590, 1480, 1430~1390, 1250, 1100, 1010, 690 |
| 2 (e) | φ-(CH$_2$)$_4$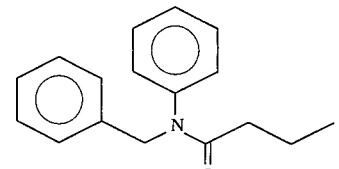 | 2-[(2S)-1-[3-[4-(4-phenylbutoxy)phenyl]propenoyl]pyrrolidin-2-yl-2-oxoacetic acid ethyl ester | Rf 0.40 (EtOAc:hexane = 1:1) | 2940, 2850, 1720, 1620, 1590, 1500, 1420, 1300, 1240, 1170, 1045, 820, 740, 690 |
| 2 (f) | 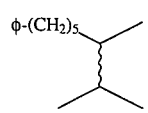 | 2-[(2S)-1-[3-(N-benzyl-N-t-butylcarbamoyl)propanoyl]pyrrolidin-2-yl]-2-oxoacetic acid ethyl ester | Rf 0.48 (EtOAc) | 2970, 1720, 1630, 1395, 1355, 1310, 1255, 1190, 1130, 1050 |
| 2 (g) | | 2-[(2S)-1-[3-(N-benzyl-N-phenylcarbamoyl)propanoyl]pyrrolidin-2-yl]-2-oxoacetic acid ethyl ester | Rf 0.49 (EtOAc) | 2965, 1720, 1630, 1400, 1355, 1260, 1195, 1130, 1050 |
| 2 (h) | φ-(CH$_2$)$_5$ | 2-[(2S)-1-[(2RS)-2-isopropyl-7-phenylheptanoyl]pyrrolidin-2-yl]-2-oxoacetic acid ethyl ester | Rf 0.44 & 0.40 (hexane:EtOAc = 7:3) | 3000~2900, 2850, 1720, 1620, 1430, 1260, 1050, 740, 690 |

TABLE III-continued

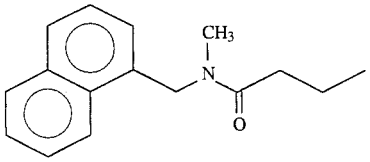

| Example No. | R— | Name | TLC | IR (vcm$^{-1}$) or mp |
|---|---|---|---|---|
| 2 (i) | 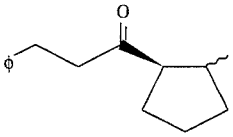 | 2-[(2S)-1-[3-[N-(1-naphthyl) methyl-N-methylcarbamoyl] propanoyl]pyrrolidin-2-yl]-2-oxoacetic acid ethyl ester | Rf 0.28 (EtOAc) | (CHCl$_3$ solution) 2950, 1715, 1625, 1430, 1250~1200, 1040 |
| 2 (j) | 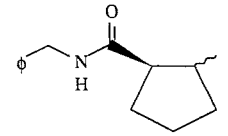 | 2-[(2S)-1-[1RS,2R)-2-(3-phenylpropanoyl) cyclopentanecarbonyl]pyrrolidin-2-yl]-2-oxoacetic acid ethyl ester | Rf 0.74 (EtOAc) | 2900, 2840, 1700, 1620, 1430, 1260, 1050, 740, 690 |
| 2 (k) | 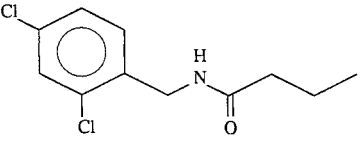 | 2-[(2S)-1-[(1RS,2R)-2-(N-benzylcarbamoyl) cylopentanecarbonyl]pyrrolidin-2-yl]-2-oxoacetic acid ethyl ester | Rf 0.45 & 0.52 (EtOAc) | 3300, 2950, 2840, 1720, 1660~1610, 1530, 1440, 1260~1240, 1130, 1050 |
| 2 (l) | 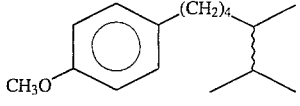 | 2-[(2S)-1-[3-[N-(2,4-dichlorophenylmethyl)carbamoyl] propanoyl]pyrrolidin-2-yl]-2-oxoacetic acid ethyl ester | Rf 0.26 (EtOAc) | (CHCl$_3$ Solution) 3450, 2950, 1720, 1650, 1620, 1500, 1430, 1260~1200, 1090, 1040 |
| 2 (m) | 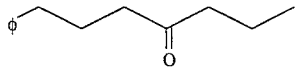 | 2-[(2S)-1-[(2RS)-2-isopropyl-6-(4-methoxyphenyl)hexanoyl]pyrrolidin-2-yl]-2-oxoacetic acid ethyl ester | Rf 0.55 & 0.62 (EtOAc:hexane = 1:1) | 2940, 1720, 1620, 1500, 1430, 1290~1240, 1050~1030, 820 |
| 2 (n) | 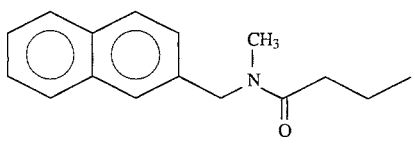 | 2-[(2S)-1-(4-oxo-7-phenylheptanoyl)pyrrolidin-2-yl]-2-oxoacetic acid ethyl ester | Rf 0.60 (EtOAc:benzene = 1:1) | 1710, 1620, 1420, 1250, 1040, 740, 690 |
| 2 (o) | 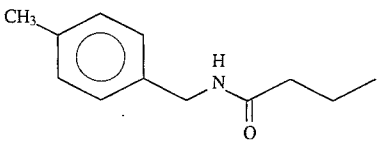 | 2-[(2S)-1-[3-[N-(2-naphthyl) methyl-N-methylcarbamoyl] propanoyl]pyrrolidin-2-yl]-2-oxoacetic acid ethyl ester | Rf 0.32 (EtOAc) | 3000~2900, 1720~1710, 1620, 1420~1400, 1250, 1100, 1040, 810, 740 |
| 2 (p) | 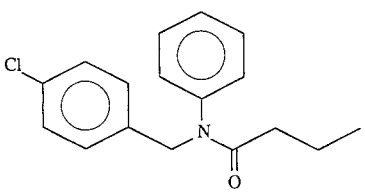 | 2-[(2S)-1-[3-[N-(4-methylphenylmethyl)carbamoyl] propanoyl]pyrrolidin-2-yl]-2-oxoacetic acid ethyl ester | Rf 0.54 (CH$_2$Cl$_2$:CH$_3$OH = 10:1) | 3300, 2980~2910, 1720, 1630, 1530, 1440, 1260, 1050 |
| 2 (q) |  | 2-[(2S)-1-[3-N-(4-chlorophenylmethyl)-N-phenylcarbamoyl]propanoyl] pyrrolidin-2-yl]-2-oxoacetic acid ethyl ester | Rf 0.31 (CH$_2$Cl$_2$:CH$_3$OH = 10:1) | 2980, 2870, 1725, 1660~1630, 1595, 1490, 1425, 1400, 1265, 1205, 1135, 1090, 1055, 1015, 800, 780, 700 |

TABLE III-continued

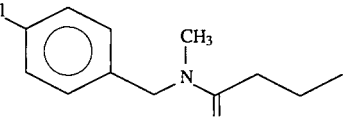

| Example No. | R— | Name | TLC | IR (vcm⁻¹) or mp |
|---|---|---|---|---|
| 2 (r) | 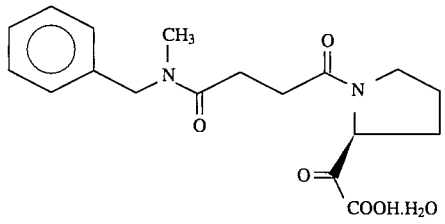 | 2-[(2S)-1-[3-[N-(4-chlorophenylmethyl)-N-methylcarbamoyl]propanoyl] pyrrolidin-2-yl]-2-oxoacetic acid ethyl ester | Rf 0.24 (EtOAc) | 2950, 2850, 1710, 1620, 1480–1400, 1250, 1105–1050, 1000, 790 |
| 2 (s) | 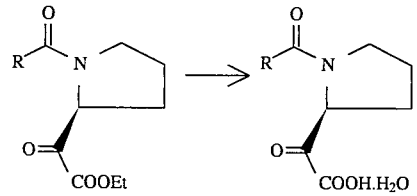 | 2-[(2S)-1-[6-(2-napthyl)methyl-oxohexanoyl]pyrrolidin-2-yl]-2-oxoacetic acid ethyl ester | Rf 0.44 (EtOAc:hexane = 2:1) | 1700, 1610, 1420, 1250, 1050, 810, 740 |

EXAMPLE 3

Synthesis of 2-[(2S)-1-[3-(N-benzyl-N-methylcarbamoyl) propanoyl]pyrrolidin-2-yl)-2-oxoacetic acid monohydrate

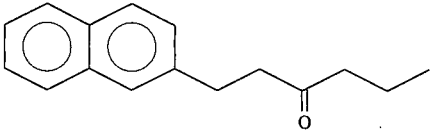

A mixture of 2-[(2S)-1-[3-(N-benzyl-N-methylcarbamoyl) propanoyl]pyrrolidin-2-yl]-2-oxoacetic acid ethyl ester (626 mg), potassium carbonate (277 mg), methanol (7 ml) and water (4 ml) was stirred for 1 hr. at room temperature. Water was added to the reaction solution. The mixture was extracted with EtOAc. The extract was washed, dried and evaporated to give the title compound (458 mg) having the following physical data:

TLC : Rf 0.42 (EtOAc : AcOH : $H_2O$)=3 :1 : 1);

IR (CHCl₃ Solution):

ν 3000, 1725, 1625, 1445 cm⁻¹

EXAMPLE 3(a)–3(r)

By the same procedure as is described in example 3, title compounds having the physical date shown in table IV were obtained.

TABLE IV

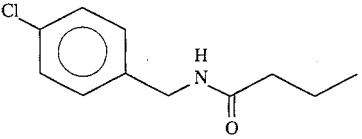

| Example No. | R- | Name | TLC | IR (vcm$^{-1}$) or mp |
|---|---|---|---|---|
| 3 (a) | 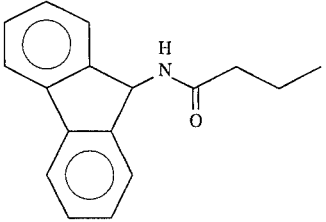 | 2-[(2S)-1-[3-[N-(4-chlorophenylmethy)carbamoyl]propanoyl]pyrrolidin-2-yl]-2-oxoacetic acid | Rf 0.35 (EtOAc:AcOH:H$_2$O = 3:1:1) | mp 160~162° C. |
| 3 (b) | 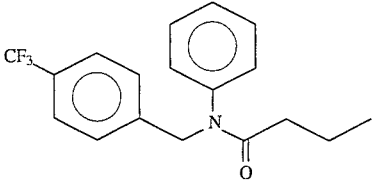 | 2-[(2S)-1-[3-[N-(9-fluorenyl)carbamoyl]propanoyl]pyrrolidin-2-yl]-2-oxacetic acid | Rf 0.44 (EtOAc:AcOH:H$_2$O = 3:1:1) | mp 212~215° C. |
| 3 (c) | 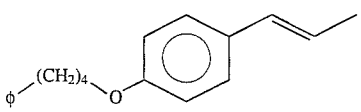 | 2-[(2S)-1-[3-[N-(4-trifluoromethylphenylmethyl)-N-phenylcarbamoyl]propanoyl]pyrrolidin-2-yl]-2-oxoacetic acid | Rf 0.10 (CHCl$_3$:CH$_3$OH = 9:1) | 3400~3300, 2890~2840, 1720, 1630~1600, 1590, 1490, 1440~1400, 1320, 1160, 1105, 1060, 1010, 700 |
| 3 (d) | φ-(CH$_2$)$_9$- | 2-[(2S)-1-(10-phenyldecanoyl)pyrrolidin-2-yl]-2-oxoacetic acid | Rf 0.10 (CHCl$_3$:CH$_3$OH = 9:1) | 3000~2840, 1720, 1580, 1440, 1230, 1030, 690 |
| 3 (e) | 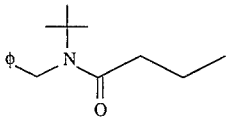 | 2-[(2S)-1-[3-[4-(4-phenylbutoxy)phenyl]propenoyl]pyrrolidin-2-yl]-2-oxoacetic acid | Rf 0.15 (CHCl$_3$:CH$_3$OH = 4:1) | 3000~2800, 1710, 1630, 1590, 1500, 1420, 1240, 1160, 810, 680 |
| 3(f) | 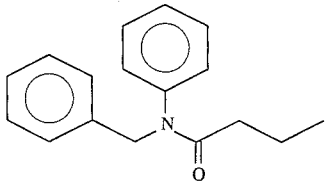 | 2-[(2S)-1-[3-(N-benzyl-N-t-butylcarbamoyl)propanolyl]pyrrolidin-2-yl]-2-oxoacetic acid | Rf 0.49 (EtOAc:AcOH:H$_2$O = 3:1:1) | (CHCl$_3$ Solution) 2975, 1725, 1630, 1445, 1405, 1355, 1185 |
| 3 (g) | 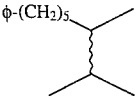 | 2-[(2S)-1-[3-(N-benzyl-N-phenylcarbamoyl)propanoyl]pyrrolidin-2-yl]-2-oxoacetic acid | Rf 0.49 (EtOAc:AcOH:H$_2$O = 3:1:1) | (CHCl$_3$ Solution) 2990, 1725, 1635, 1595, 1495, 1405 |
| 3 (h) | φ-(CH$_2$)$_5$- | 2-[(2S)-1-[(2RS)-2-isopropyl-7-phenylheptanoyl]pyrrolidin-2-yl]-2-oxoacetic acid | Rf 0.08 (CHCl$_3$:CH$_3$OH = 9:1) | (CHCl$_3$ Solution) 3300~2920, 2850, 1720, 1590, 1420, 1320, 1420~1200, 1040 |
| 3 (i) | 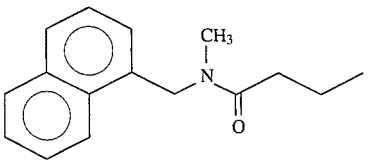 | 2-[(2S)-1-[3-[N-(1-naphthyl)methyl-N-methylcarbamoyl]propanoyl]pyrrolidin-2-yl]-2-oxoacetic acid | Rf 0.05 (CHCl$_3$:CH$_3$OH = 9:1) | (KBr tablet) 3300~3000, 2900, 1720, 1630~1590, 1430~1400, 1230, 1030, 790, 760 |

TABLE IV-continued

| Example No. | R- | Name | TLC | IR (vcm⁻¹) or mp |
|---|---|---|---|---|
| 3 (j) | φ-CH₂CH₂-C(=O)- cyclopentyl | 2-[(2S)-1-[(1RS,2R)-2-(3-phenylpropanoyl)cyclopentanecarbonyl]pyrrolidin-2-yl]-2-oxoacetic acid | Rf 0.08 (CHCl₃:CH₃OH = 9:1) | (KBr tablet) 3500~3400, 2950, 1690, 1580, 1440, 690 |
| 3 (k) | φ-CH₂-NH-C(=O)- cyclopentyl | 2-[(2S)-1-[(1RS,2R)-2-(N-benzylcarbamoyl)cyclopentanecarbonyl]pyrrolidin-2-yl]-2-oxoacetic acid | Rf 0.05 (CHCl₃:CH₃OH = 9:1) | (KBr tablet) 3500~3300, 2950, 1720, 1610, 1440, 1240, 1040, 690 |
| 3 (l) | 2,4-dichlorobenzyl-NH-C(=O)-CH₂CH₂- | 2-[(2S)-1-[3-[N-(2,4-dichlorophenylmethyl)carbamoyl]propanoyl]pyrrolidin-2-yl]-2-oxoacetic acid | Rf 0.05 (CHCl₃:CH₃OH = 9:1) | (KBr tablet) 3500~3300, 2950, 2900, 1720, 1620, 1440, 1250, 1040, 820 |
| 3 (m) | 4-CH₃O-C₆H₄-(CH₂)₄-CH(iPr)- | 2-[(2S)-1-[(2RS)-2-isopropyl-6-(4-methoxyphenyl)hexanoyl]pyrrolidin-2-yl]-2-oxoacetic acid | Rf 0.10 (CHCl₃:CH₃OH = 9:1) | 3500~3300, 2900, 1740~1720, 1600~1580, 1500, 1440, 1230, 1020, 810, 730, 690 |
| 3 (n) | φ-CH₂CH₂CH₂-C(=O)-CH₂CH₂- | 2-[(2S)-1-(4-oxo-7-phenylheptanoyl)pyrrolidin-2-yl]-2-oxoacetic acid | Rf 0.16 (EtOAc:CH₃OH = 4:1) | (KBr tablet) 3460, 1700, 1570, 1400, 1250, 1180, 730, 690 |
| 3 (o) | 2-naphthyl-CH₂-N(CH₃)-C(=O)-CH₂CH₂- | 2-[(2S)-1-[3-[N-(2-naphthyl)methyl-N-methylcarbamoyl]propanyl]pyrrolidin-2-yl]-2-oxoacetic acid | Rf 0.60 (EtOAc:AcOH: H₂O = 3:1:1) | (KBr tablet) 3500~3400, 2900, 1710, 1610, 1430, 1230 |
| 3 (p) | 4-CH₃-C₆H₄-CH₂-NH-C(=O)-CH₂CH₂- | 2-[(2S)-1-[3-[N-(4-methylphenylmethylcarbamoyl]propanoyl]pyrrolidin-2-yl]-2-oxoacetic acid | Rf 0.50 (EtOAc:AcOH: H₂O = 3:1:1) | (CHCl₃ Solution) 2990, 2880, 1725, 1640, 1595, 1490, 1400, 1265, 1095, 1045, 1015 |
| 3 (q) | 4-Cl-C₆H₄-CH₂-N(C₆H₅)-C(=O)-CH₂CH₂- | 2-[(2S)-1-[3-[N-(4-chlorophenylmethyl)-N-phenylcarbamoyl]propanoyl]pyrrolidin-2-yl]-2-oxoacetic acid | Rf 0.56 (EtOAc:AcOH: H₂O = 3:1:1) | (KBr tablet) 3300, 2920, 1730, 1605, 1560, 1460, 1110, 1240, 1190, 1110, 1060, 1035 |
| 3 (r) | 4-Cl-C₆H₄-CH₂-N(CH₃)-C(=O)-CH₂CH₂- | 2-[(2S)-1-[3-[N-(4-chlorohenylmethyl)-N-methylcarbamoyl]propanoyl]pyrrolidin-2-yl]-2-oxoacetic acid | Rf 0.10 (CHCl₃:CH₃OH = 9:1) | (CHCl₃ Solution) 2950~2840, 1710, 1620, 1430, 1390, 1080 |

EXAMPLE 4

Synthesis of 2-[(2S)-1-[3-(N-benzyl-N-methylcarbamoyl) propanoyl]pyrrolidin-2-yl]1-2-oxo-N-ethylacetamide

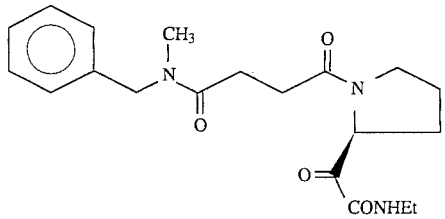

A solution of 2[(2S)-1-[3-(N-benzyl-N-methylcarbamoyl) propanoyl)pyrrolidin-2-yl)-2-oxoacetic acid (98 mg) in THF (3 ml) was cooled to −20° C. Triethylamine (188 µl) and isobutyl chloroformate (77 µl) were added dropwise to the solution. The mixture was stirred for 20 mins at the same temperature. An aq. solution of ethylamine (70%; 200 µl) was added dropwise to the solution at the same temperature. The solution was stirred for 1 hr, while the temperature of the solution was raised to room temperature gradually. Water was added to the reaction solution. The mixture was extracted with EtOAc. The extract was washed, dried and evaporated. The residue was purified by column chromatography on silica gel ($CH_2Cl_2$—$CH_3OH$) to give the title compound (62 mg) having the following physical data:

TLC : Rf 0.34 (EtOAc: AcOH : $H_2O$=3 : 1 : 1);

IR : ν3300, 2980, 2940, 2875, 1730, 1630, 1520, 1435, 1375, 1355, 1240, 1145, 1120, 1040 $cm^{-1}$

EXAMPLE 4(a)–4(b)

By the same procedure as is described in example 4, title compounds having the physical data shown in Table V were obtained.

EXAMPLE 5

Synthesis of (2RS)-2-[(2S)-1-(3-(N-benzyl-N-methylcarbamoyl) propanoyl)pyrrolidin-2-yl)-2-hydroxyacetic acid monohydrate

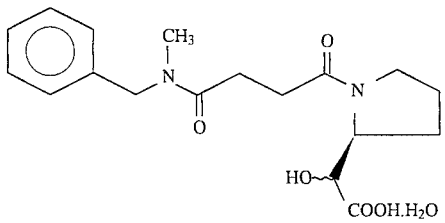

By the same procedure as is described in example 3, using (2RS)-2-[(2S)-1-13-(N-benzyl-N-methylcarbamoyl)propanoyl)pyrrolidin-2-yl)-2-hydroxyacetic acid ethyl ester (670 mg), the title compound (517 mg) having the following physical data was given.:

TLC : Rf 0.42 (EtOAc : AcOH : $H_2O$=3 : 1 : 1);

IR ($CHCl_3$ solution):

ν 3000, 1725, 1625, 1440 $cm^{-1}$

TABLE V

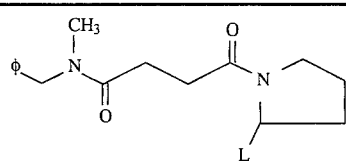

| Example No. | L — | Name | TLC | IR (ν$cm^{-1}$) |
|---|---|---|---|---|
| 4 (a) | O=C(CONH$_2$) | 2-[(2S)-1-[3-(N-benzyl-N-methylcarbamoyl)propanoyl]pyrrolidin-2-yl]-2-oxoacetamide | Rf 0.37 ($CH_2Cl_2$:$CH_3OH$) = 10:1) | ($CHCl_3$ Solution) 3540, 3500, 3410, 2990, 2870, 1700, 1620, 1560, 1435, 1240~1200 |
| 4 (b) | O=C(CON(CH$_3$)φ) | 2-[(2S)-1-[3-(N-benzyl-N-methylcarbamoyl)propanoyl]pyrrolidin-2-yl]-2-oxo-N-methyl-N-benzylacetamide | Rf 0.19 (EtOAc) | 2920, 1725, 1630, 1435, 1240, 1110, 1070, 1040 |

EXAMPLE 6

Synthesis of
(2RS)-2-1(2S)-1-[3-(N-benzyl-N-methylcarbamoyl)
propanoyl]pyrrolidin-2-yl]1-2-hydroxyacetic acid
benzyl ester

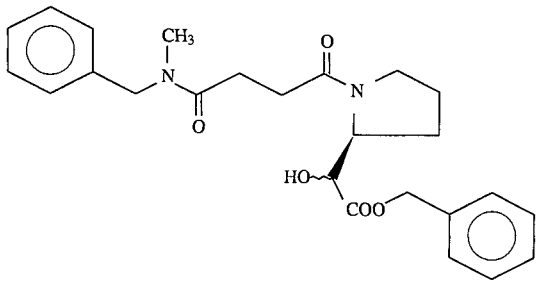

A mixture of (2RS)-2-[(2S)-1-[3-(N-benzyl-N-methlcarbamoyl) propanoyl)pyrrolidin-2-yl)-2-hydroxyacetic acid (134 mg), potassium carbonate (64 mg), benzyl bromide (51 μl) and DMSO (1 ml) was stirred for 1 hr at room temperature. Water was added to the mixture. The mixture was extracted with a mixture of hexane and EtOAc (1:1). The extract was washed, dried and evaporated. The residue was purified by column chromatography on silica gel (hexane-EtOAc) to give the title compound (141 mg) having the following physical data:

TLC : Rf 0.46 (CH$_2$Cl$_2$ : CH$_3$OH=1 : 1);

IR (KBr tablet):

v3400–3340, 2950–2920, 1735, 1625, 1440–1410, 1240, 1185, 1120 cm$^{-1}$

EXAMPLE 6(a)

By the same procedure as is described in example 6, title compound having the physical data shown in table VI was given.

EXAMPLE 7

Synthesis of
2-[(2S)-1-[3-(N-benzyl-N-methylcarbamoyl)
propanoyl]pyrrolidin-2-yl]-2-oxoacetic acid benzyl
ester By the same procedure as is described in example 2, using (2RS)-2-[(2S)-1-[3-(N-benzyl-N-methylcarbamoyl)propanoyl)pyrrolidin-2-yl]-2-hydroxyacetic acid benzyl ester (129 mg), the title compound (109 mg) having the following physical data was given:

TLC : Rf 0.56 (CH$_2$Cl$_2$ : CH$_3$OH=10 : 1);

IR : v2950–2910, 1720, 1630, 1435, 1260, 1120, 1050 cm$^{-1}$

TABLE VI

| Example No. | Formula | Name | TLC | IR (vcm$^{-1}$) |
|---|---|---|---|---|
| 6 (a) |  | 2-[(2S)-1-[3-(N-benzyl-N-methylcarbamoyl)propanoyl]pyrrolidin-2-yl]-2-oxoacetic acid isobutyl ester | Rf 0.24 (EtOAc) | 2950, 2870, 1720, 1635, 1435, 1260, 1120, 1055, 735, 695 |

EXAMPLE 8

Synthesis of
(1RS)-1-(2S)-1-13-(N-benzyl-N-methylcarbamoyl)
propanoyl]pyrrolidin-2-yl)-2,2,2-trifluoroethanol

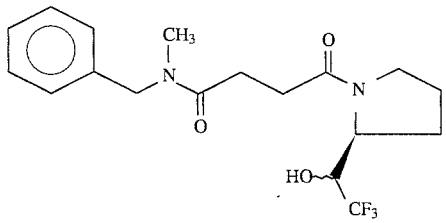

Trifluoroiodomethane (2.3 g) was cooled to −78° C. with a trap. DMF (7 ml), (2S)-1-[3-(N-benzyl-N-methylcarbamoyl)propanoyl]pyrrolidin-2-al (710 mg) and zinc (1.0 g) were added thereto. And the mixture was treated with ultrasonic waves for 2 hrs. at room temperature. 1N hydrochloric acid was added to the reaction solution. The mixture was extracted with EtOAc. The extract was washed, dried, and evaporated. The residue was purified by column chromatography on silica gel (hexane - EtOAc) to give the title compound (217 mg) having the following physical data:

TLC:Rf 0.24 & 0.33 (EtOAc);

IR:ν 3300~2250, 2920, 1735, 1690, 1640~1610, 1440~1400, 1375, 1265, 1160, 1120 cm$^{-1}$

EXAMPLE 9

Synthesis of
1-[(2S)-1-[3-(N-benzyl-N-methylcarbamoyl)
propanoyl]pyrrolidin-2-yl]-2,2,2-t
rifluoroethan-1-one

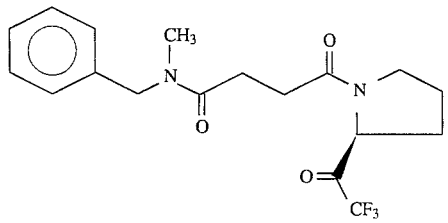

A mixture of (1RS)-1-[(2S)-1-13-(N-benzyl-N-methylcarbamoyl) propanoyl]pyrrolidin-2-yl ]-2,2,2-trifluoroethanol (103 mg), Dess-Martin reagent (435 mg) and methylene chloride (1.5 ml) was stirred for 3 hrs. at room temperature. After reaction, the raction solution was diluted with ether. The diluted solution was added dropwise to a saturated aq. solution of sodium bicarbonate (30 ml) wherein sodium thiosulfate (3.0 g) was dissolved. The mixture was stirred for 10 mins at room temperature. The mixture was extracted with EtOAc. The extract was washed, dried and evaporated. The residue was purified by column chromatography on silica gel (hexane - EtOAc) to give the title compound (52 mg) having the following physical data:

TLC:Rf 0.32 (EtOAc);

IR:ν 3270~3150, 2920, 1730, 1630~1600, 1445~1405, 1260~1240, 1160 cm$^{-1}$

EXAMPLE 10

Synthesis of
(3RS)-3-[(2S)-1-(3-(N-benzyl-N-methylcarbamoyl)
propanoyl]pyrrolidin-2-yl)-3-hydroxypropionic acid
ethyl ester

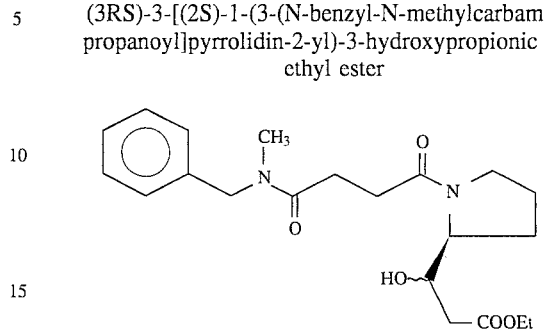

Zinc powder (482 mg) and a small amount of iodine were added to a solution of ethyl bromoacetate (0.70 ml) in THF (6 ml). The mixture was refluxed for 30 mins. The solution was added dropwise to a solution of (2S)-1-[3-(N-benzyl-N-methylcarbamoyl)propanoyl)pyrrolidin- 2-al (1.21 g) in benzene (10 ml). The mixture was refluxed for 30 mins. After reaction, 1N hydrochloric acid was added to the mixture. The mixture was extracted with EtOAc. The extract was washed, dried, and evaporated. The residue was purified by column chromatography on silica gel (hexane-EtOAc) to give the title compound (1.21 g) having the following physical data:

TLC:Rf 0.38 (CH$_2$Cl$_2$:CH$_3$OH=10:1);

IR:ν 3450~3350, 2980, 1730, 1630, 1440~1410, 1375, 1270~1240, 1180~1150, 1110, 1030 cm$^{-1}$

EXAMPLE 11

Synthesis of
3-[(2S)-1-(3-(N-benzyl-N-methylcarbamoyl)propanoyl]
pyrrolidin-2-yl]-3-oxopropionic acid ethyl ester

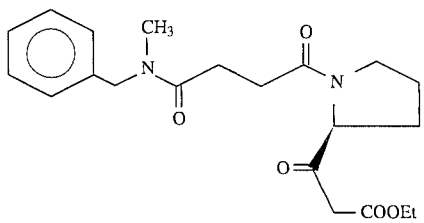

A solution of (3RS)-3-[(2S)-1-[3-(N-benzyl-N-methylcarbamoyl) propionyl]pyrrolidin-2-yl]-3-hydroxypropionic acid ethyl ester (230 mg) in acetone (1 ml) was cooled to −30° C. Excess Jones' reagent was added dropwise to the solution. The mixture was stirred for 1 hr at the same temperature, and for 1 hr at −20° C., and for 1 hr at −10° C. Isopropyl alcohol was added to the reaction solution. Water was added to the mixture. The mixture was extracted with EtOAc. The extract was washed, dried, and evaporated. The residue was purified by column chromatography on silica gel (hexane-EtOAc) to give the title compound (98 mg) having the following physical data:

TLC:Rf 0.50 (CH$_2$Cl$_2$:CH$_3$OH=10:1);

IR:ν 2980~2920, 1710, 1630, 1430~1400, 1360, 1305, 1255, 1020 cm$^{-1}$

EXAMPLE 12

Synthesis of
(3RS)-3-[(2S)-1-[3-(N-benzyl-N-methylcarbamoyl)
propanoyl]pyrrolidin-2-yl]-3-hydroxy-2,2-
difluoropropionic acid ethyl ester

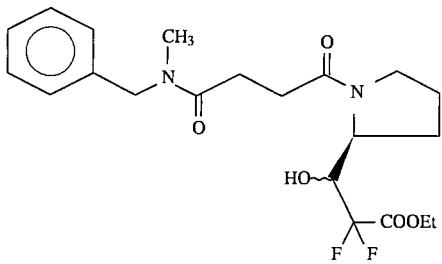

A mixture of zinc powder (520 mg) and THF (8 ml) was refluxed. A solution of ethyl bromo difluoroacetate (815 μl) in THF (6 ml) was added dropwise to the solution. The mixture was refluxed for 2 mins. A solution of (2S)-1-[3-(N-benzyl-N-methylcarbamoyl)propanoyl]pyrrolidin-2-al (800 mg) in THF (8 ml) was added dropwide to the solution. The mixture was refluxed for 10 mins. After cooling, a saturated aq. solution of sodium bicarbonate was added to the solution. The mixture was extracted with EtOAc. The extract was washed, dried and evaporated. The residue was purified by column chromatography on silica gel (hexane-EtOAc) to give the title compound (754 mg) having the following physical data:

TLC:Rf 0.21 (EtOAc);

IR:ν 3270~3200, 3000, 2925, 1780~1760, 1635~1605, 1440~1425, 1375, 1310 cm$^{-1}$

EXAMPLE 13

Synthesis of
3-[(2S)-1-[3-(N-benzyl-N-methylcarbamoyl)
propanoyl]pyrrolidin-2-yl]-3-oxo-2,
2-difluoropropionic acid ethyl ester

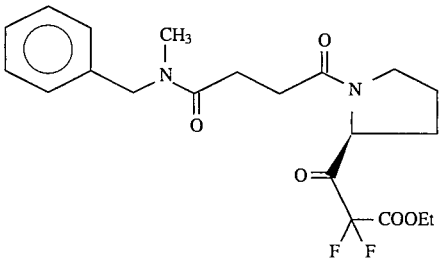

A solution of (3RS)-3-[(2S)-1-[3-(N-benzyl-N-methylcarbamoyl) propanoyl)pyrrolidin-2-yl)-3-hydroxy-2,2-difluoropropionic acid ethyl ester (250 mg) in methylene chloride (1.5 ml) was added dropwise to a suspension of Dess-Martin reagent (448 mg) in methylene chloride (6 ml). The mixture was stirred for 3 hrs. The reaction mixture was diluted with ether. A saturated aq. solution of sodium bicarbonate (30 ml) wherein sodium thiosulfate (2.26 g) was dissolved was added to the diluted solution. The mixture was stirred for 10 mins, and extracted with EtOAc. The extract was washed, dried and evaporated. The residue was purified by column chromatography on silica gel (hexane - EtoAc) to give the title compound (238 mg) having the following physical data:

TLC:Rf 0.25 (EtOAc);

IR:ν 3000~2930, 1765, 1630, 1435, 1370, 1200, 1125, 1085, 1015 cm$^{-1}$

EXAMPLE 14

Synthesis of
3-[(2S)-1-[3-(N-benzyl-N-methylcarbamoyl)
propanoyl]pyrrolidin-2-yl]-3-oxo-2,2-
difluoropropionic acid monohydrate

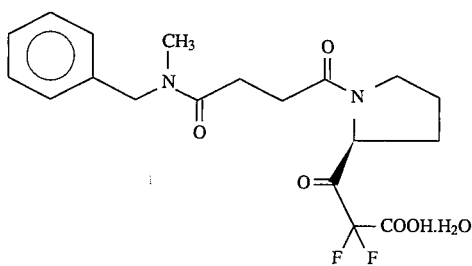

By the same procedure as is described in Example 3, using 3-[( 2S)-1-[3-(N-benzyl-N-methylcarbamoyl)propanoyl]pyrrolidin-2-yl]-3-oxo- 2,2-difluoropropionic acid ethyl ester, the title compound having the following physical data was given:

TLC:Rf 0.4. EtOAc:AcOH:H$_2$O=3:1:1);

IR (CHCl$_3$ Solution):

ν2990, 2920, 1755, 1625, 1440, 1120 cm$^{-1}$

EXAMPLE 15

Synthesis of (1RS)-1-[(2S)-1-[3-(N-benzyl-N-
methylcarbamoyl)propanoyl]
pyrrolidin-2-yl)-propan-1-o l

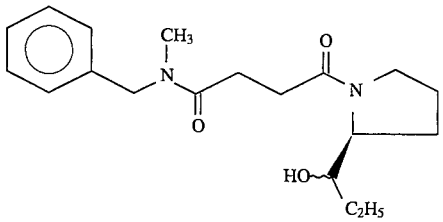

A solution of (2S)-1-[3-(N-benzyl-N-methylcarbamoyl-)propanoyl]pyrrolidin-2-al (700 mg) in THF (5 ml) was cooled to −25° C. A solution of ethyl magnesium chloride in THF (2M, 1.5 ml) was added dropwise to the solution. The mixture was stirred for 30 mins at the same temperature, and for 30 mins at 0° C. and further 1 hr. at room temperature. After reaction, a saturated aq. solution of ammonium chloride was added to the mixture. The oily layer separated was washed, dried and evaporated. The residue was purified by column chromatography on silica gel (EtOAc - CH$_3$OH) to give the title compound (270 mg) having the following physical data:

TLC:Rf 0.47 (EtOAc:CH$_3$OH=9:1));

IR:ν3350, 1600, 1400, 1220, 1090, 720, 680 cm$^{-1}$

EXAMPLE 15(a)

By the same procedure as is described in example 15, the title compound having the physical data shown in table VII was obtained.

TABLE VII

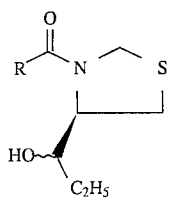

| Example No. | Fromula | Name | TLC | IR (vcm$^{-1}$) |
|---|---|---|---|---|
| 15 (a) |  | (1RS)-1-[(4R)-3-[1-(3-phenylpropanoyl)pieridin-2-yl carbonyl]thiazolidin-4-yl]propan-1-ol | Rf 0.30 (EtOAc:hexane = 1:1) | 3400, 1610, 1400, 1240, 1150, 1000, 740, 670 |

EXAMPLE 16

Synthesis of 1-1(2S)-1-[3-(N-benzyl-N-methyl carbamoyl)propanoyl) pyrrolidin-2-yl)propan-1-one

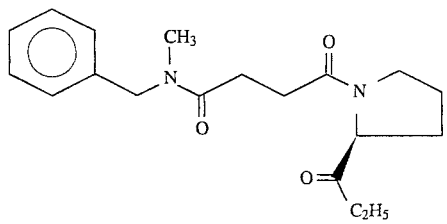

By the same procedure as is described in example 2, using (1RS)-1-[(2S)-1-[3-(N-benzyl-N-methylcarbamoyl)propanoyl]pyrrolidin-2-yl]propan-1-ol, the title compound having the following physical data was given:

TLC:Rf 0.49 (CH$_2$Cl$_2$:CH$_3$OH=19:1);

IR:v 1700, 1620, 1400, 1100, 720, 670 cm$^{-1}$

EXAMPLE 17

Synthesis of (1RS)-1-phenyl-1-[(2S)-1-[3-(N-benzyl-N-methylcarbamoyl) propanoyl)pyrrolidin-2-yl]methanol

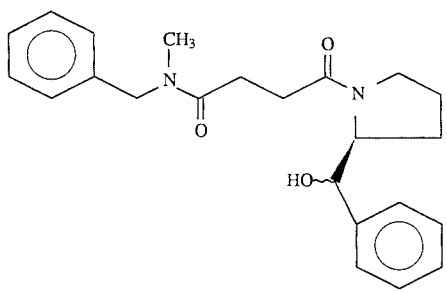

A solution of (2S)-1-[3-(N-benzyl-N-methylcarbamoyl)propanoyl]pyrrolidin-2-al (200 mg) in THF (5 ml) was cooled to −25° C. A solution of phenyl magnesium bromide in THF (2M, 0.49 ml) was added dropwise to the solution. The reaction solution was stirred for 30 mins, at the same temperature, and for 30 mins at 0° C. A saturated aq. solution of ammonium chloride was added to the reaction solution. The mixture was extracted with EtOAc. The extract was washed, dried, and evaporated. The residue was purified by column chromatography on silica gel (EtOAc-CH$_3$OH) to give the title compound (45 mg) having the following physical data:

TLC:Rf 0.47 (EtOAc:CH$_3$OH:19:1);

IR:v3350, 1610, 1420, 1180, 1040, 670 cm$^{-1}$

EXAMPLE 17(a)–17(c)

By the same procedure as is described in example 17, title compounds having the physical data shown in table VIII were obtained.

TABLE VII

R—C(=O)—N (thiazolidine ring with HO-CH(φ)- substituent at 4-position)

| Example No. | Formula | Name | Formula | IR (vcm$^{-1}$) |
|---|---|---|---|---|
| 17 (a) | φ-(CH$_2$)$_3$-C(=O)-N (thiazolidine) | (1RS)-1-phenyl-1-[(4R)-3-[(4R)-3-(4-phenylbutanoyl)thiazolidin-4-ylcarbonyl]thiazolidin-4-yl]methanol | Rf 0.31 (EtOAc:hexane = 1:1) | (KBr tablet) 3400, 1620, 1400, 730, 690 |
| 17 (b) | φ-CH$_2$-N(CH$_3$)-C(=O)-(CH$_2$)$_2$- | (1RS)-1-phenol-1-[(4R)-3-[3-(N-benzyl-N-methylcarbamoyl)propanoyl]thiazolidin-4-yl]methanol | Rf 0.25 (EtOAc:hexane = 4:1) | (KBr tablet) 3350, 1610, 1390, 720, 690 |
| 17 (c) | φ-(CH$_2$)$_3$-C(=O)-NH-CH(iPr)- | (1RS)-1-phenyl-1-[(4R)-3-[(2RS)-2-(4-phenylbutanoylamino)-3-methylbutanoyl]thiazolidin-4-yl]methanol | Rf 0.59 (EtOAc:hexane = 2:1) | (KBr tablet) 3400, 3270, 1610, 1410, 730, 690 |

EXAMPLE 8

Synthesis of [(2S)-1-[3-(N-benzyl-N-methylcarbamoyl)propanoyl]pyrrolidin-2-yl]dimethoxymethane

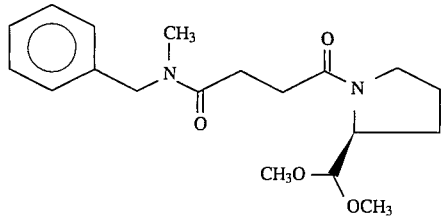

α-Camphorsulphonic acid (11.6 mg) was added to a solution of (2S)-1-[3-(N-benzyl-N-methylcarbamoyl)propanoyl]pyrrolidin-2-al (160 mg) in methanol (2 ml). The mixture was stirred for 3 hrs. at room temperature. After reaction, the mixture was extracted with EtOAc. The extract was washed, dried, and evaporated. The residue was purified by column chromatography on silica gel (EtOAc—CH$_2$Cl$_2$—CH$_3$OH) to give the title compound (156 mg) having the following physical data:

TLC:Rf 0.42 (EtOAc:CH$_2$Cl$_2$:CH$_3$OH=9:5:1);

IR:ν 2900, 1620, 1400, 1180, 1110, 1050, 960, 730, 690 cm$^{-1}$

EXAMPLE 18(a)–18(b)

By the same procedure as is described in example 18, title compounds having the physical data shown in table IX were obtained.

TABLE IX

R—C(=O)—N (thiazolidine ring with CH$_3$O-, OCH$_3$ substituents)

| Example No. | R- | Name | TLC | IR (vcm$^{-1}$) |
|---|---|---|---|---|
| 18 (a) | φ-CH$_2$-N(CH$_3$)-C(=O)-(CH$_2$)$_2$- | [(4R)-3-[3-(N-benzyl-N-methylcarbamoyl)propanoyl]thiazolidin-4-yl]dimethoxymethane | Rf 0.38 (EtOAc: CH$_2$Cl$_2$: CH$_3$OH) = 9:5:1) | 2910, 2820, 1730, 1650–1620, 1400, 1105, 1060, 970, 730, 690 |

TABLE IX-continued

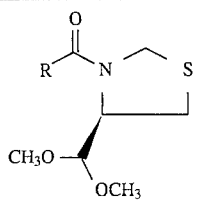

| Example No. | R- | Name | TLC | IR (vcm$^{-1}$) |
|---|---|---|---|---|
| 18 (b) | φ-(CH$_2$)$_9$— | [(4R)-3-(10-phenyldecanoyl) thiazolidin-4-yl]dimethoxymethane | Rf 0.58 (EtOAc:hexane) = 1:1) | 2900, 2830, 1640, 1420, 1390, 1100, 1060, 740, 680 |

EXAMPLE 19

Synthesis of 2-[(2S)-1-[3-(N-benzyl-N-methylcarbamoyl) propanoyl]pyrrolidin-2-yl]-1,3-dioxolane

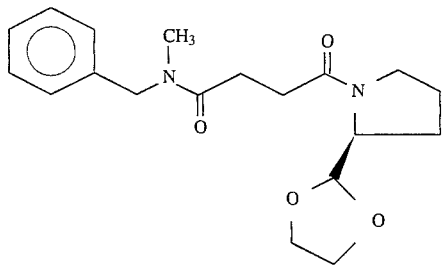

Ethylene glycol (0.3 ml), p-toluenesulphonic acid (1 mg) were added to a solution of (2S)-1-[3-(N-benzyl-N-methylcarbamoyl) propanoyl]pyrrolidin-2-al (164 mg) in benzene (3 ml). The mixture was refluxed for 1 hr. The reaction solution was poured into a saturated aq. solution of sodium bicarbonate. The mixture was extracted with benzene. The extract was washed, dried, and evaporated. The residue was purified by column chromatography on silica gel (CH$_3$OH-EtOAc-CH$_2$Cl$_2$) to give the title compound (79 mg) having the following physical data:

TLC:Rf 0.35 (CH$_3$OH:EtOAc:CH$_2$Cl$_2$=1:9:5));

IR:ν2900, 2850, 1720, 1620, 1400, 1110, 1050, 720, 680 cm$^{-1}$

EXAMPLE 20

Synthesis of 3-[(2S)-1-[3-(N-benzyl-N-methylcarbamoyl) propanoyl]pyrrolidin-2-yl]-3-oxopropionic acid monohydrate

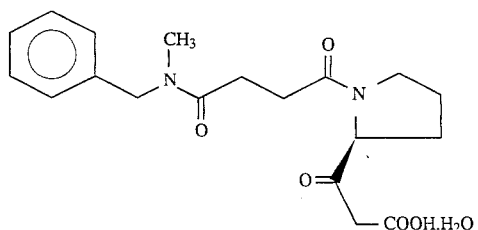

By the same procedure as is described in example 3, using the compound prepared in example 11, the title compound having the following physical data was obtained:

TLC:Rf 0.62 (EtOAc:AcOH:H$_2$O=3:1:1);

IR (CHCl$_3$ Solution):

ν3000, 1725, 1630, 1440, 1410, 1250~1210 cm$^{-1}$

FORMULATION EXAMPLE

The following components were admixed by a conventional method and punched out to obtain 100 tablets each containing 50 mg of active ingredient.

| | |
|---|---|
| (2RS)-2-[(2S)-N-[3-(N-benzyl-N-methylcarbamoyl) propanoyl]pyrrolidin-2-yl]-2-hydroxyacetic acid ethyl ester | 5 g |
| Cellulose calcium glycolate (disintegrating agent) | 0.2 g |
| Magnesium stearate (lubricating agent) | 0.1 g |
| Microcrystaline cellulose | 4.7 g |

What is claimed is:
1. A pyrrolidine derivative of the formula:

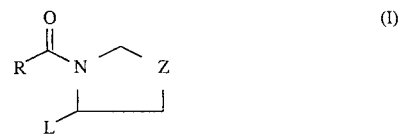

wherein Z represents a methylene group, R represents the general formula:

G—E—D—B—A— wherein A represents a linkage which contains no atom, an alkylene group of from 1 to 6 carbon atoms(s), an alkenylene group of from 2 to 6 carbon atoms, a group of the formula:

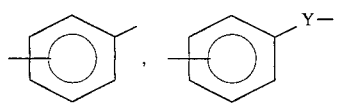

wherein Y represents an alkylene group of from 1 to 4 carbon atom(s) or an alkenylene group of from 2 to 4 carbon atoms, a saturated hydrocarbon ring of from 4 to 7 carbon atoms or a heterocyclic mono ring containing 3 to 7 ring members including 1 or 2 hetero atom(s) selected from N, O and S atoms which may be partially or fully saturated or aromatic, B represents a linkage which contains no atom or an alkylene group of from 1 to 6 carbon atom(s), D represents a group of the formula:

—NR¹—CO— wherein R¹ represents a hydrogen atom, an alkyl group of from 1 to 6 carbon atom(s), a phenyl group or a benzyl group, E represents a linkage which contains no atom, an alkylene group of from 1 to 8 carbon atom(s) or an alkylene group of from 1 to 8 carbon atom(s) substituted or by a phenyl or benzyl group, G represents a mono-, bi- or tri-carbocyclic ring(s) containing not more than 15 carbon atoms which may be partially or fully saturated or aromatic, or mono-, bi- or tri-heterocyclic ring(s) containing not more than 15 ring members including carbon and 1 or 2 hetero atoms selected from N, O and S atoms which may be partially or fully saturated or aromatic wherein said carbocyclic or heterocyclic ring(s) represented by G is unsubstituted or substituted by 1–3 of an alkyl group of from 1 to 6 carbon atoms(s), an alkoxy group of from 1 to 6 carbon atom(s), a halogen atom, a trifluoromethyl group or a nitro group, and L represents a group of the formula:

—CO—COR²

—CO—CH₂—COR²

—CO—CF₂—COR²

—CO—CO—NR⁵R⁶ or

—CO—CH₂—CO—NR⁵R⁶ wherein, R² represents a hydrogen atom, a hydroxy group, an alkyl group of from 1 to 6 carbon atom(s), an alkoxy group of from 1 to carbon atom(s), a phenyl group, an alkyl group of from 1 to 6 carbon atom(s) substituted by a phenyl group, or an alkoxy group of from 1 to 6 carbon atom(s) substituted by a phenyl group, R⁵ and R⁶ independently represent a hydrogen atom, an alkyl group of from 1 to 6 carbon atom(s), a phenyl group, or an alkyl group of from 1 to 6 carbon atom(s) substituted by a phenyl group, with the proviso that the following compounds are excluded:

(i) compounds wherein both of A and B are a linkage which contains no atom or a non-toxic salt or hydrate thereof.

2. A compound according to claim 1, wherein G is phenyl, naphthyl or fluorenyl group which is unsubstituted or substituted.

3. A compound according to claim 1, of general formula:

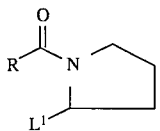

(Ia)

wherein L¹ represents a group of general formula:

—CO—CH₂—COR²

—CO—CF₂—COR²

—CO—CO—NR⁵R⁶ or wherein all of the symbols are the same meaning as defined in claim 1.

4. A compound according to claim 1 or 3, which is:

3-((2S)-1-{3-(N-benzyl-N-methylcarbamoyl)propanoyl)pyrrolidin- 2-yl)-3-oxopropionic acid or ethyl ester thereof, 3-((2S)-1-{3-(N-benzyl-N-methylcarbamoyl)propanoyl)pyrrolidin-2-yl}-3-oxo-2, 2-difluoropropionic acid or ethyl ester thereof, 2-{(2S)-1-{3-(N-benzyl-N-methylcarbamoyl)propanoyl)pyrrolidin-2 yl} -2-oxo-N-ethylacetamide, 2-{(2S-1-{3-(N-benzyl-N-methylcarbamoyl)propanoyl}pyrrolidin-2-yl}-2-oxoacetamide or 2-{(2S)-1-{3-(N-benzyl-N-methylcarbamoyl)propanoyl)pyrrolidin-2-yl} -2-oxo-N-methyl-N-benzylacetamide.

5. A compound according to claim 1 of general formula:

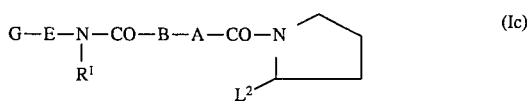

(Ic)

—CO—COR² wherein all of the symbols are the same meaning as defined in claim 1.

6. A compound according to claim 1 or 5, which is:

2-{(2S)-1-{3-(N-benzyl-N-methylcarbamoyl)propanoyl}pyrrolidin- 2-yl)-2-oxoacetic acid, 2-{(2S)-1-{3-{N-(4-chlorophenylmethyl)carbamoyl}propanoyl}pyrrolidin-2-yl}-2-oxoacetic acid, 2-{(2S)-1-{3-{N-(9-fluorenyl)carbamoyl}propanoyl}pyrrolidin-2-yl }-2-oxoacetic acid, 2-{(2S)-1-{3-{N-(4-trifluoromethylphenylmethyl)-N-phenylcarbamoyl propanoyl}pyrrolidin-2-yl}-2-oxoacetic acid, 2-{(2S)-1-(3-(N-benzyl-N-t-butylcarbamoyl)propanoyl}pyrrolidin-2-yl}-2-oxoacetic acid, 2-{(2S)-1-{3-(N-benzyl-N-phenylcarbamoyl}propanoyl}pyrrolidin- 2-yl}-2-oxoacetic acid, 2-{(2S)-1-{3-{N-(1-naphthy)methyl-N-methylcarbamoyl) propanoyl)pyrrolidin-2-yl)-2-oxocetic acid, 2-{(2S)-1-{3-{N-(2,4-dichlorophenylmethyl)carbamoyl}propanoyl}pyrrolidin-2-yl)-2-oxoacetic acid, 2-{(2S-1-{3-(N-(2-naphthyl)methyl-N-methylcarbamoyl} propanyl}pyrrolidin-2-yl}-2-oxoacetic acid, 2-{(2S)-1-{(1RS, 2R)-2-(N-benzylcarbamoyl)cyclopentanecarbonyl}pyrrolidin-2-yl}-2-oxoacetic acid, 2-{(2S)-1-{3-{N-(4-methylphenylmethyl)carbamoyl}propanoyl} pyrrolidin-2-yl)-2-oxoacetic acid, 2-{(2S)-1-{3-{N-(4-chlorophenylmethyl)-N-phenylcarbamoyl}propanoyl}pyrrolidin-2-yl)-2-oxoacetic acid or 2-{(2S)-1-{3-{N-(4-chlorophenylmethyl)-N-methylcarbamoyl}propanoyl}pyrrolidin-2-yl}-2-oxoacetic acid 2-{(2S)-1-(3-(N-benzyl-N-methylcarbamoyl)propanoyl}pyrrolidin-2-yl}-2-hydroxyacetic acid, 2-{(2S)-1-{3-(N-(4-chlorophenylmethyl)carbamoyl}propanoyl}pyrrolidin-2-yl)-2-hydroxyacetic acid, 2-{(2S)-1-{3-{N-(9-fluorenyl)carbamoyl}propanoyl}pyrrolidin-2-yl}-2-hydroxyacetic acid, {(2S)-1-{3-(N-benzyl-N-methylcarbamoyl)propanoyl}pyrrolidin-2-yl} dimethoxymethane, 2-{(2S)-1-{3-(N-benzyl-N-methylcarbamoyl)propanoyl}pyrrolidin-2-yl}-2-1,3-dioxolan, (1RS)-1-{(2S)-1-(3-(N-benzyl-N-methylcarbamoyl)propanoyl}pyrrolidin-2-yl}propan-1-ol or (1RS)-1-phenyl-1-{(2S)-1-{3-(N-benzyl-N-methylcarbamoyl) propanoyl}pyrrolidin-2-yl)methanol] .

7. A compound which is:

2-{(2S)-1-{(1RS, 2R)-2-(3-phenylpropanoyl)cyclopentanecarbonyl}pyrrolidin-2-yl}-2-oxoacetic acid or ethyl ester thereof.

8. A compound which is:

2-{(2S)-1-{3-(4-(4-phenylbutoxy)phenyl}propenoyl}pyrrolidin-2-yl}-2-oxoacetic acid or ethyl ester thereof.

9. A pharmaceutical composition for treating amnesia which comprises, as active ingredient, a therpeutically effective amount of pyrrolidine derivative of the following general formula (I) and pharmaceutically acceptable carrier and/or coating:

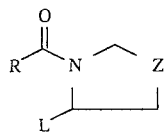 (I)

wherein Z represents a methylene group, R represents the general formula:

G—E—D—B—A— wherein A represents a linkage which contains no atom, an alkylene group of from 1 to 6 carbon atoms(s), an alkenylene group of from 2 to 6 carbon atoms, a group of the formula:

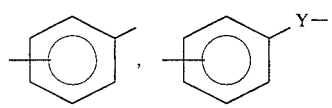

wherein Y represents an alkylene group of from 1 to 4 carbon atom(s) or an alkenylene group of from 2 to 4 carbon atoms, a saturated hydrocarbon ring of from 4 to 7 carbon atoms or a heterocyclic mono ring containing 3 to 7 ring members including 1 or 2 hetero atom(S) selected from N, O and S atoms which may be partially or fully saturated or aromatic, B represents a linkage which contains no atom or an alkylene group of from 1 to 6 carbon atom(s), D represents a group of the formula:

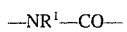

—NR$^1$—CO— wherein R$^1$ represents a hydrogen atom, an alkyl group of from 1 to 6 carbon atom(s), a phenyl group or a benzyl group, E represents a linkage which contains no atom, an alkylene group of from 1 to 8 carbon atom(s) or an alkylene group of from 1 to 8 carbon atom(s) substituted or by a phenyl or benzyl group, G represents a mono-, bi- or tri-carbocyclic ring(s) containing not more than 15 carbon atoms which may be partially or fully saturated or aromatic, or mono-, bi- or tri-heterocyclic ring(s) containing not more than 15 ring members including carbon and 1 or 2 hetero atoms selected from N, O and S atoms which may be partially or fully saturated or aromatic wherein said carbocyclic or heterocyclic ring(s) represented by G is unsubstituted or substituted by 1–3 of an alkyl group of from 1 to 6 carbon atoms(s), an alkoxy group of from 1 to 6 carbon atom(s), a halogen atom, a trifluoromethyl group or a nitro group, and L represents a group of the formula:

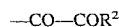
—CO—COR$^2$

—CO—CH$_2$—COR$^2$

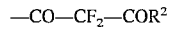
—CO—CF$_2$—COR$^2$

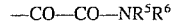
—CO—CO—NR$^5$R$^6$ or

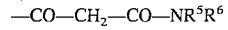
—CO—CH$_2$—CO—NR$^5$R$^6$ wherein, R$^2$ represents a hydrogen atom, a hydroxy group, an alkyl group of from 1 to 6 carbon atom(s), an alkoxy group of from 1 to 6 carbon atom(s), a phenyl group, an alkyl group of from 1 to 6 carbon atom(s) substituted by a phenyl group, or an alkoxy group of from 1 to 6 carbon atom(s) substituted by a phenyl group, R$^5$ and R$^6$ independently represent a hydrogen atom, an alkyl group of from 1 to 6 carbon atom(s), a phenyl group, or an alkyl group of from 1 to 6 carbon atom(s) substituted by a phenyl group, with the proviso that compounds wherein both of A and B are a linkage which contains no atom are excluded; or a non-toxic salt or hydrate thereof.

10. A method for prevention and treatment of amnesia which comprises administration of a therapeutically effective amount of pyrrolidine derivative of the general formula (I):

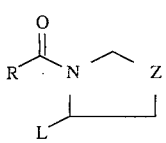 (I)

wherein Z represents a methylene group, R represents the general formula:

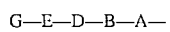

G—E—D—B—A— wherein A represents a linkage which contains no atom, an alkylene group of from 1 to 6 carbon atoms(s), an alkenylene group of from 2 to 6 carbon atoms, a group of the formula:

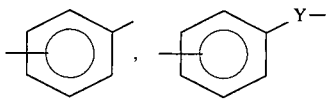

wherein Y represents an alkylene group of from 1 to 4 carbon atom(s) or an alkenylene group of from 2 to 4 carbon atoms, a saturated hydrocarbon ring of from 4 to 7 carbon atoms or a heterocyclic mono ring containing 3 to 7 ring members including 1 or 2 hetero atom(s) selected from N, O and S atoms which may be partially or fully saturated or aromatic, B represents a linkage which contains no atom or an alkylene group of from 1 to 6 carbon atom(s), D represents a group of the formula:

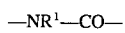

—NR$^1$—CO— wherein R$^1$ represents a hydrogen atom, an alkyl group of from 1 to 6 carbon atom(s), a phenyl group or a benzyl group, E represents a linkage which contains no atom, an alkylene group of from 1 to 8 carbon atom(s) or an alkylene group of from 1 to 8 carbon atom(s) substituted or by a phenyl or benzyl group, G represents a mono-, bi- or tri-carbocyclic ring(s) containing not more than 15 carbon atoms which may be partially or fully saturated or aromatic, or mono-, bi- or tri-heterocyclic ring(s) containing not more than 15 ring members including carbon and 1 or 2 hetero atoms selected from N, O and S atoms which may be partially or fully saturated or aromatic wherein said carbocyclic or heterocyclic ring(s) represented by G is unsubstituted or substituted by 1–3 of an alkyl group of from 1 to 6 carbon atoms(s), an alkoxy group of from 1 to 6 carbon atom(s), a halogen atom a trifluoromethyl group or a nitro group, and L represents a group of the formula:

—CO—COR$^2$

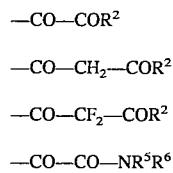

—CO—CH$_2$—COR$^2$

—CO—CF$_2$—COR$^2$

—CO—CO—NR$^5$R$^6$ or

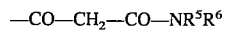

—CO—CH$_2$—CO—NR$^5$R$^6$ wherein, R$^2$ represents a hydrogen atom, a hydroxy group, an alkyl group of from 1 to 6 carbon atom(s), an alkoxy group of from 1 to 6 carbon atom(s), a phenyl group, an alkyl group of from 1 to 6 carbon atom(s) substituted by a phenyl group, or an alkoxy group of from 1 to 6 carbon atom(s) substituted by a phenyl group,, R$^5$ and R$^6$ independently represent a hydrogen atom, an alkyl group of from 1 to 6 carbon atom(s), a phenyl group, or an alkyl group of from 1 to 6 carbon atom(s) substituted by a phenyl group, with the proviso that compounds wherein both of A and B are a linkage which contains no atom are excluded; or a non-toxic salt or hydrate thereof.

* * * * *

UNITED STATES PATENT AND TRADEMARK OFFICE
CERTIFICATE OF CORRECTION

PATENT NO. : 5,545,657
DATED : August 13, 1996
INVENTOR(S) : Masaaki Toda et al

It is certified that error appears in the above-indentified patent and that said Letters Patent is hereby corrected as shown below:

| | | | |
|---|---|---|---|
| Column 51, | line 42, | after "to" | insert --6--. |
| Column 52, | line 3, | after "or" | insert -- -CO-CH$_2$-CO-NR$^5$R$^6$ --; |
| | line 28, | insert --wherein L$^2$ represents a group of general formula:--. | |
| Column 53, | line 4, | after "acid" insert --.-- | |
| | delete lines 5 - 26. | | |

Signed and Sealed this

Twenty-eighth Day of January, 1997

Attest:

BRUCE LEHMAN

Attesting Officer   Commissioner of Patents and Trademarks